(12) United States Patent
Khankal et al.

(10) Patent No.: US 10,273,204 B2
(45) Date of Patent: *Apr. 30, 2019

(54) PROCESS FOR CONVERSION OF DIMETHYL SULFIDE TO METHYL MERCAPTAN

(71) Applicant: Chevron Phillips Chemical Company LP, The Woodlands, TX (US)

(72) Inventors: Reza Khankal, Humble, TX (US); Henry Hwu, Houston, TX (US); Daniel M. Hasenberg, Kingwood, TX (US); Christina M. Barry, Houston, TX (US); Mitchell D. Refvik, Kingwood, TX (US); Michael S. Hankinson, Lake Jackson, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/241,562

(22) Filed: Aug. 19, 2016

(65) Prior Publication Data
US 2018/0050986 A1 Feb. 22, 2018

(51) Int. Cl.
*C07C 319/06* (2006.01)
*B01J 8/02* (2006.01)

(52) U.S. Cl.
CPC ........... *C07C 319/06* (2013.01); *B01J 8/0278* (2013.01); *B01J 8/0285* (2013.01); *B01J 2208/00407* (2013.01); *B01J 2208/027* (2013.01)

(58) Field of Classification Search
CPC .... C07C 319/06; C07C 319/26; C07C 319/08
See application file for complete search history.

(56) References Cited

U.S. PATENT DOCUMENTS

| 2,667,515 | A | * | 1/1954 | Beach | C07C 321/00 568/70 |
|---|---|---|---|---|---|
| 2,796,438 | A | | 6/1957 | Martin et al. | |
| 2,820,831 | A | | 1/1958 | Doumani | |
| 2,822,400 | A | | 2/1958 | Cinque et al. | |
| 2,822,401 | A | * | 2/1958 | Hoot | B01J 21/00 568/71 |
| 2,829,171 | A | | 4/1958 | Doumani | |
| 3,081,353 | A | | 3/1963 | Galliate | |
| 3,488,739 | A | * | 1/1970 | Venrooy | B01J 27/04 568/60 |
| 3,792,094 | A | | 2/1974 | Hanson | |
| 3,880,933 | A | * | 4/1975 | Kubicek | C07C 319/02 568/70 |
| 4,005,149 | A | | 1/1977 | Kubicek | |
| 4,059,636 | A | * | 11/1977 | Kubicek | C07C 319/06 568/61 |
| 4,313,006 | A | | 1/1982 | Hager | |
| 4,396,778 | A | | 8/1983 | Hager | |
| 5,866,721 | A | | 2/1999 | Hofen et al. | |
| 7,576,243 | B2 | | 8/2009 | Barth et al. | |
| 2008/0200730 | A1 | | 8/2008 | Barth et al. | |
| 2017/0342028 | A1 | | 11/2017 | Pichai et al. | |

OTHER PUBLICATIONS

Luyben (A Feed-Effluent Heat Exchanger/Reactor Dynamic Control Laboratory Experiment:, Chemical Engineering Education, Winter 2000, pp. 56-61 and 73).*
Material Safety Data Sheet, "Aluminum Oxide Vitrified Product," MSDS No. ALVIT001, Jul. 31, 2007, 4 pages, Norton.
Safety Data Sheet, "DOWTHERM™ G Heat Transfer Fluid," Apr. 16, 2015, 12 pages, The Dow Chemical Company.
Foreign communication from the corresponding International Application No. PCT/US2017/047334, International Search Report and Written Opinion, Nov. 3, 2017, 12 pages.
Office Action dated Mar. 1, 2018 (16 pages) of U.S. Appl. No. 15/604,995, entitled "Process for Producing Methyl Mercaptan from Dimethyl Sulfide" filed May 25, 2017 by Pichai, et al.

* cited by examiner

*Primary Examiner* — Rosalynd A Keys
(74) *Attorney, Agent, or Firm* — Conley Rose, P.C.

(57) ABSTRACT

Disclosed herein are systems and processes involving the catalyzed cleavage reaction of dimethyl sulfide to methyl mercaptan. The catalyzed cleavage reaction can be a standalone system or process, or can be integrated with a methyl mercaptan production plant.

23 Claims, 4 Drawing Sheets

PROCESS FOR CONVERSION OF DIMETHYL SULFIDE TO METHYL MERCAPTAN

TECHNICAL FIELD

This disclosure relates to the conversion of dimethyl sulfide to methyl mercaptan.

BACKGROUND

Methyl mercaptan (MeSH) can be produced on a commercial scale via the following reaction in the presence of a catalyst:

$$\text{methanol}(CH_3OH) + \text{hydrogen sulfide}(H_2S) \rightarrow \text{methyl mercaptan}(CH_3SH) + \text{water}(H_2O).$$

Examples of processes for producing MeSH by reacting hydrogen sulfide and methanol are described in U.S. Pat. Nos. 2,822,400 and 3,792,094. Depending on the purity of the feedstocks and reaction conditions, a reaction effluent can include the desired methyl mercaptan and other compounds which can include but are not limited to methanol (MeOH), hydrogen sulfide ($H_2S$), hydrogen ($H_2$), carbon monoxide (CO), carbon dioxide ($CO_2$), light hydrocarbons, dimethyl sulfide (DMS), dimethyl disulfide (DMDS), water ($H_2O$), mercaptans with a higher carbon number than MeSH, or combinations thereof. Processes for producing methyl mercaptan can include various separation techniques for isolating the methyl mercaptan from any of the above mentioned compounds in the reaction effluent, as well as separation techniques for isolating any of the compounds from one another. Various streams can be obtained by the separation techniques, for example, a stream containing mostly DMS, a stream containing mostly $H_2S$, and a stream containing mostly MeSH can be recovered from the processes.

DMS in particular can be present in the reaction effluent as a by-product of the reactions. For example, DMS can be produced via the following reactions in the presence of the same catalyst:

$$\text{methanol}(CH_3OH) + \text{methyl mercaptan}(CH_3SH) \rightarrow \text{dimethyl sulfide}(DMS) + \text{water}(H_2O)$$

or $$\text{methyl mercaptan}(2CH_3SH) \rightarrow \text{dimethyl sulfide}(DMS) + \text{hydrogen sulfide}(H_2S).$$

Historically, formation of DMS has been less desirable than formation of MeSH. However, depending on operating conditions, the amount of DMS produced can still exceed 10 wt % of the MeSH produced in the reactions. While DMS can have some value at certain purities under certain market conditions, thus justifying isolation of DMS in a stream dedicated for DMS recovery, MeSH can have a higher value. Moreover, even when it is desired to isolate and recover DMS, prices can fall due to oversupply.

SUMMARY

Disclosed herein is a process for the conversion of dimethyl sulfide to methyl mercaptan, comprising contacting dimethyl sulfide with a catalyst in the presence of an excess amount of hydrogen sulfide in a reactor to yield a reactor effluent comprising methyl mercaptan, hydrogen sulfide, and carbon disulfide, wherein the catalyst comprises alumina, NiMo on an alumina support, CoMo on an alumina support, or a combination thereof.

Also disclosed herein is a system comprising a DMS stream comprising dimethyl sulfide received from a methyl mercaptan production plant, a $H_2S$ stream comprising hydrogen sulfide received from the methyl mercaptan production plant, a combined feed stream comprising dimethyl sulfide received from the DMS stream and hydrogen sulfide received from the $H_2S$ stream, a preheater which receives the combined feed stream and yields a heated feed stream comprising the dimethyl sulfide and hydrogen sulfide at a reaction temperature, a reactor receiving the heated feed stream, wherein the reactor contains a catalyst comprising alumina, NiMo on an alumina support, CoMo on an alumina support, or a combination thereof, a reactor effluent stream receiving reactor effluent from the reactor, wherein the reactor effluent comprises methyl mercaptan in an amount of about 5 mole % to about 76 mole % based on the total moles of methyl mercaptan, dimethyl sulfide, carbon disulfide, and dimethyl disulfide in the reactor effluent stream.

Further disclosed herein is a process comprising utilizing a methyl mercaptan production plant to recover dimethyl sulfide, responsive to a first market condition, contacting at least a portion of the recovered dimethyl sulfide with a CoMo or NiMo catalyst in the presence of hydrogen sulfide in a reactor to yield a reactor effluent comprising methyl mercaptan, hydrogen sulfide, and carbon disulfide, responsive to a second market condition, discontinuing the contacting of the recovered dimethyl sulfide in the reactor, and selling all or a portion of the recovered dimethyl sulfide.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
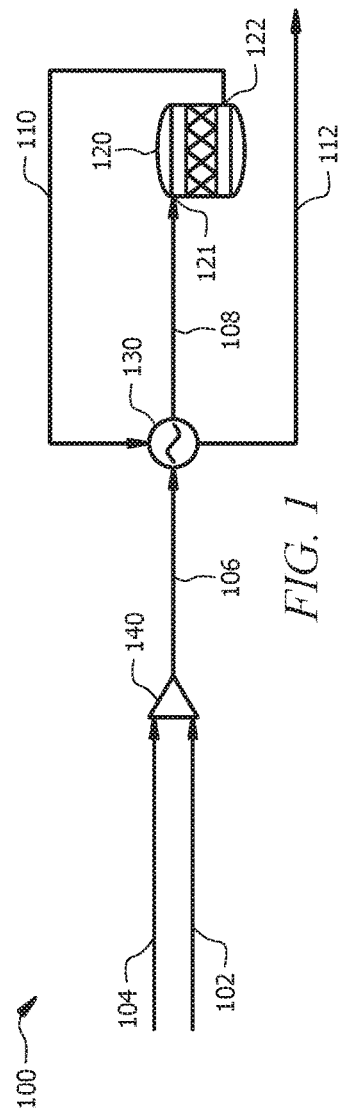
FIG. 1 illustrates a system for converting dimethyl sulfide to methyl mercaptan in which one or more of the disclosed processes are performed.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The figures described above and the written description of specific structures and functions below are not presented to limit the scope of what Applicants have invented or the scope of the appended claims. Rather, the figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the figures and are not intended to limit the scope of the invention or the appended claims.

Within the scope of the system and processes disclosed herein, it is contemplated that various equipment associated with separation systems (e.g., valves, pumps, accumulators, piping, reboilers, condensers, heaters, compressors, control systems, safety equipment, and the like), while may not be shown for purposes of clarity, can be included in various aspects according to techniques known in the art with the aid of this disclosure.

Systems and processes for the conversion of dimethyl sulfide to methyl mercaptan are disclosed. Dimethyl sulfide (DMS) can be converted to methyl mercaptan (MeSH) via the following reaction when in contact with a catalyst:

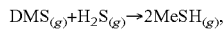

$$DMS_{(g)} + H_2S_{(g)} \rightarrow 2MeSH_{(g)}.$$

This reaction can be referred to herein as the "DMS cleavage reaction." The DMS cleavage reaction is slightly endothermic with a ΔH of 5200 BTU/lbmol DMS, thus heating of the reactor to maintain reaction temperature is generally required. Because the reactants are DMS and hydrogen sulfide ($H_2S$), streams of DMS and $H_2S$ are obtained as feeds to the reactor (also referred to as the "DMS cleavage reactor"). The DMS feedstock for the disclosed systems and processes can be obtained from a methyl mercaptan production process via separation techniques which isolate and recover DMS. The $H_2S$ feedstock for the disclosed systems and processes can be obtained from recycled $H_2S$ in a methyl mercaptan production plant or from another refinery process. According to aspects of the disclosure, the MeSH product (e.g., in a reactor effluent) obtained from the DMS cleavage reaction can be further processed to recover MeSH or can be recycled to a methyl mercaptan production plant. It is contemplated that the reactor effluent from the DMS cleavage reaction can be further processed to remove most of the $H_2S$ in the reactor effluent, and the remaining components can be recycled to a methyl mercaptan production plant.

The processes of the disclosure are described concurrently with the description of the figures.

Turning now to the figures, FIG. 1 illustrates a system 100 for converting dimethyl sulfide to methyl mercaptan. The system 100 in FIG. 1 can be referred to herein as a "DMS cleavage system" and any processes performed using the system 100 can be referred to herein as a "DMS cleavage process."

The DMS cleavage system 100 can include one or more of DMS stream 102, a $H_2S$ stream 104, a mixing device 140, a combined feed stream 106, a preheater 130, a heated feed stream 108, a reactor 120, a reactor effluent stream 110, and a cooled effluent stream 112.

The DMS stream 102 and the $H_2S$ stream 104 can be mixed in the mixing device 140 to form the combined feed stream 106 containing the contents of both the DMS stream 102 and the $H_2S$ stream 104. The combined feeds stream 106 can be heated in a preheater 130 to the temperature of the DMS cleavage reaction in the reactor 120. The heated feed stream 108 can flow from the preheater 130 to the reactor 120, where at least some of the DMS can be converted to MeSH under DMS cleavage reaction conditions in the presence of a catalyst described hereinbelow. Reactor effluent can flow from the reactor 120 in reactor effluent stream 110 to the preheater 130, where the reactor effluent can be cooled. The cooled effluent can flow in the cooled reactor effluent stream 112 for further processing (see FIG. 2) or for recycle to a methyl mercaptan production plant (see FIG. 3).

The DMS stream 102 can be a stream received from a methyl mercaptan production plant. The composition of the DMS stream 102 is such that DMS is present in an amount of about 0.80, 0.85, 0.90, 0.95, or more mole fraction based on the total moles of components in the DMS stream 102. The DMS stream 102 can contain other components found in the methyl mercaptan production plant, such as methyl mercaptan (MeSH) and $CS_2$. For example, MeSH can be present in an amount of less than about 0.20, 0.15, 0.10, 0.05, or less mole fraction based on the total moles of components in the DMS stream 102. In an aspect, no MeSH is present in the DMS stream 102. $CS_2$ can be present in an amount of less than about 0.05, 0.04, 0.03, 0.02, 0.01, or less mole fraction based on the total moles of components in the DMS stream 102. It is contemplated the DMS stream 102 can also contain minor amounts (less than 0.0001 mole fraction based on the total moles of components in the DMS stream 102) of one or more of hydrogen, methane, $CO_2$, $H_2S$, methanol, water, and dimethyl disulfide (DMDS). In an aspect, the DMS stream 102 is in the vapor phase.

The $H_2S$ stream 104 can be a $H_2S$ feedstock used as a feed for both a methyl mercaptan production plant (e.g., plant 210 of FIG. 3 or FIG. 4) and the reactor 120 of system 100. Additionally or alternatively, the $H_2S$ stream 104 can include $H_2S$ (with other components depending upon any purification steps) received from a methyl mercaptan production plant or any other process. The composition of the $H_2S$ stream 104 is such that $H_2S$ is present in an amount of about 0.95, 0.96, 0.97, 0.98, 0.99, or more mole fraction based on the total moles of components in the $H_2S$ stream 104. The $H_2S$ stream 104 can contain other components such as methane and $CO_2$. For example, methane can be present in an amount of less than about 0.01, 0.009, 0.008, 0.007, 0.006, 0.005, 0.004, 0.003, 0.002, 0.001, or less mole fraction based on the total moles of components in the $H_2S$ stream 104. $CO_2$ can be present in an amount of less than about 0.005, 0.004, 0.003, 0.002, 0.001, or less mole fraction based on the total moles of components in the $H_2S$ stream 104. It is contemplated that the $H_2S$ stream 104 can also contain minor amounts (less than 0.0001 mole fraction per component based on the total moles of components in the $H_2S$ stream 104) of one or more of hydrogen, MeSH, DMS, methanol, water, dimethyl disulfide (DMDS), and $CS_2$. In an aspect, the $H_2S$ stream 104 is in the vapor phase. In another aspect, no MeSH is present in the $H_2S$ stream 104.

The mixing device 140 can be any device which can mix (combine) the gaseous contents of the DMS stream 102 and the $H_2S$ stream 104. The mixing device 140 can provide mixing via agitation of the flow there through. For example, the mixing device 140 can be a junction of piping where the DMS stream 102 and the $H_2S$ stream 104 meet to form the combined feed stream 106. Alternatively, the mixing device 140 can be a static mixer having fixed baffles (e.g., in a helical arrangement, or any other baffle arrangement) placed within a housing, where the baffles continuously blend the gaseous contents of the DMS stream 102 and the $H_2S$ stream 104. Alternatively, the mixing device 140 can have moving parts such as a propeller or impeller.

Dimethyl sulfide and hydrogen sulfide can be fed to the reactor 120 via the combined feed stream 106. In an aspect, the combined feed stream 106 can flow the combined gaseous contents received from the DMS stream 102 and the $H_2S$ stream 104 via the mixing device 140 to the preheater 130. $H_2S$ can be present in excess in the combined feed stream 106. For example, the mole ratio of $H_2S$ to DMS ($H_2S$:DMS) in the combined feed stream 106 can be at least 3:1; alternatively at least 5:1; alternatively, at least 10:1; alternatively, less than 100:1.

The preheater 130 can receive the combined feed stream 106. In the preheater 130, the contents of the combined feed stream 106 can be heated (where heat is transferred) by exchanging thermal energy with a heating medium (e.g., steam or the contents of another process stream). The preheater 130 can have any configuration to heat the combined feed stream 106. For example, the preheater 130 can have a shell and tube configuration in which the heating medium passes through the preheater 130 in tubes (on the tube side thereof) while the combined feed stream 106 passes through the preheater 130 on a shell side thereof. Alternatively, the heating medium can pass through the shell side of preheater 130, and the combined feed stream 106 can pass through the tubes of the preheater. In an aspect, the heating medium can be the reactor effluent stream 110 as shown in FIG. 1. In aspects where the reactor effluent stream 110 is the heating medium for heating the combined feed stream 106, the preheater 130 can be referred to as a cross-flow heat exchanger.

In an aspect, the DMS cleavage system 100 can include additional heaters (e.g., electric or steam heaters) in combination with the preheater 130 in heating the combined feed stream 106 to reaction temperature for the reactor 120, to yield the heated feed stream 108.

The heated feed stream 108 receives heated contents from the preheater 130. Heating the combined feed stream 106 can form heated feed stream 108 containing the same contents as the combined feed stream 106, except the heated feed stream 108 can have a higher temperature than combined feed stream 106. The temperature of the heated feed stream 108 can be any of the operating temperatures for the reactor 120 disclosed herein. For example, the temperature of the heated feed stream 108 can be in a range of about 275° C. (527° F.) to about 305° C. (563° F.). $H_2S$ can be present in excess in the heated feed stream 108. For example, the mole ratio of $H_2S$ to DMS ($H_2S$:DMS) in the heated feed stream 108 is the same as the combined feed stream 106, e.g., at least 3:1, alternatively, at least 5:1; alternatively, at least 10:1.

The heated feed stream 108 comprising the heated mixture of DMS and $H_2S$ can flow to the reactor 120. Thus, the reactor 120 can receive the heated feed stream 108. The reactor 120 is configured to receive the heated feed of DMS and $H_2S$ and to convert DMS to MeSH via catalyzed cleavage reactions. The catalyzed cleavage reactions can occur by contacting DMS with a catalyst in the presence of an excess amount of hydrogen sulfide in the reactor 120 to yield a reactor effluent comprising methyl mercaptan, hydrogen sulfide, and carbon disulfide. The reactor 120 can be referred to herein as a "DMS cleavage reactor."

Figure 5:
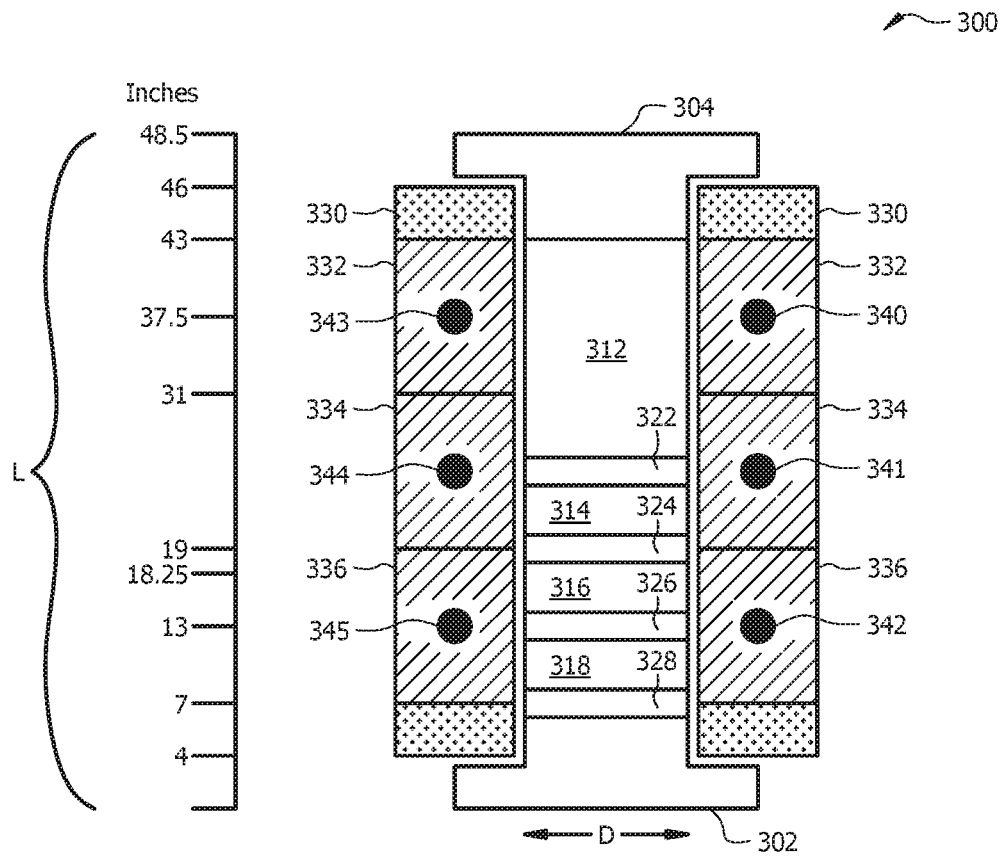
FIG. 5 illustrates a cross-sectional view of a DMS cleavage reactor.

The reactor 120 can have a reactor inlet 121 and a reactor outlet 122. The reactor 120 can be a vessel having one or more catalyst beds therein. Alternatively, the reactor 120 can be a vessel having one or more tube reactors placed therein in any suitable pattern or array. Each of the tube reactors can contain one or more catalyst beds. An example of such a tube reactor having catalyst beds is shown as the stainless steel tube reactor 300 in FIG. 5. As can be seen in FIG. 5, the tube reactor 300 has catalyst beds 312, 314, 316, and 318 stacked vertically on top of one another and separated by a layer of steel wool, 322, 324, and 326, or in the case of 328, a layer of steel wool and glass beads. In an aspect, one or more of the tube reactor 300 of FIG. 5 can be placed in a vessel of the reactor 120 of FIG. 1, with the tube reactor inlet 302 of each tube reactor 300 fluidly connected with reactor inlet 121 (e.g., via a manifold or partition inside the vessel which creates an isolated flow path for the heated feed from the reactor inlet 121 to the inlet 302 of the one or more tube reactors 300). In such as aspect, the tube reactor outlet 304 of each tube reactor 300 can fluidly connect with the reactor outlet 122 (e.g., via another manifold or partition inside the vessel which creates an isolated flow path for the reaction product from each tube reactor outlet 304 of the one or more tube reactors 300 to the reactor outlet 122). Additionally, heat can be supplied to the shell side of the tube reactor(s) 300 in the vessel of the reactor 120 by electric heaters (e.g., heater 330 of FIG. 5) or by a heat transfer fluid, such as DOWTHERM™ G. When using a heat transfer fluid, the space between each tube reactor inlet 302 and tube reactor outlet 304 can form one or more shell-side chambers in which a heat transfer fluid can contact the shell-side of the tube reactor(s) 300 so as to supply heat to the tube reactor(s) 300 in the vessel.

In aspects which include tube reactors such as tube reactor 300 in FIG. 5, the diameter of each tube reactor can range from about 1 inch to about 12 inches; alternatively, from about 1 inch to about 4 inches; alternatively, from about 1 inch to about 6 inches.

The vessel and any tube reactor(s) placed therein can be made of any material which is corrosion resistant to the components therein, such as stainless steel.

Operating temperature of the reactor 120 or each of the tube reactors 300 contained in the reactor 120 is based on the weight average temperature (WAT). The WAT is defined as $(T_{inlet}+T_{outlet})/2$, where $T_{inlet}$ is the temperature of the reactor inlet (e.g., reactor inlet 121 or tube reactor inlet 302) and $T_{outlet}$ is the temperature of the reactor outlet (e.g., reactor outlet 122 or tube reactor outlet 304). For example, the WAT of reactor 120 can be the temperature at the reactor inlet 121 plus the temperature at the reactor outlet 122, divided by 2. Alternatively, the WAT of the reactor 120 can be the average temperature for all tube reactor inlets 302 in the reactor 120 plus the average temperature for all tube reactor outlets 304 in the reactor 120, divided by 2. The WAT of each individual tube reactor 300 can be the temperature of the respective tube reactor inlet 302 plus the respective tube reactor outlet 304, divided by 2.

The WAT can range from about 265° C. to about 305° C.; alternatively, the WAT can range from about 250° C. to about 305° C.; alternatively, the WAT can range from about 280° C. to about 290° C.; alternatively, the WAT can be about 285° C. The range of temperatures for $T_{inlet}$ which provide favorable reactions are temperatures 250° C. or greater. The range of temperatures for $T_{outlet}$ which provide favorable reactions are temperatures of 305° C. or less. In certain aspects, both the $T_{inlet}$ and the $T_{outlet}$ can have a temperature in the range of from about 265° C. to about 305° C. Without being limited by theory it is believed that the selectivity of DMS to MeSH decreases and the amount of $CS_2$ formed increases at $T_{outlet}$ temperatures above 305° C.

$H_2S$ can be present in excess in the reactor 120. For example, the $H_2S$/DMS mole ratio in the reactor 120 (and/or in each tube reactor 300) can be at least 3:1, at least 5:1, or at least 10:1. Additionally, the mole ratio can be less than 100:1, less than 70:1, less than 40:1, or less than 30:1.

The weight hourly space velocity (WHSV) of DMS can range from 0.2 to 15 g DMS/g cat./hr; alternatively, 0.2 to 2 g DMS/g cat./hr.

The pressure in the reactor 120 (and thus for any tube reactor 300 therein) can be at least about 100, 150, 200, 250, 300, 350, 400, 450, or 500 psig (689, 1034, 1379, 1724, 2068, 2416, 2758, 3103, or 3447 kPa). In an aspect, the pressure is greater than about 450 psig (3103 kPa). In an additional or alternative aspect, the pressure is less than about 1000 psig (6895 kPa).

In an aspect, the reactor 120 (and/or each tube reactor 300 placed therein) can be operated with a WAT of about 285° C. to about 290° C., a WHSV of about 0.2 to about 2.0 g DMS/g cat./hr, and a mole ratio of $H_2S$ to DMS of about 3:1 to about 10:1.

The catalyst used in the DMS cleavage reaction can include alumina (referred to herein as alumina catalyst), nickel and molybdenum on an alumina support (referred to herein as NiMo catalyst), cobalt and molybdenum on an alumina support (referred to herein as CoMo catalyst), or a combination thereof. The catalyst can have Type II sites; alternatively, the catalyst may not have Type II sites. The Co or Ni and Mo can be present in the form of sulfides or oxides. If in oxide form, the NiMo or CoMo catalyst can be pre-sulfided using well known sulfiding techniques or can be used directly without prior sulfiding, since sulfiding occurs rapidly under the DMS cleavage reaction conditions. In an aspect the catalyst can be 3 wt % Co or Ni and 10 wt % Mo based on the total weight of the support, with the remainder being the alumina support. Catalysts of alumina and catalysts having Co or Ni and Mo in oxide form on an alumina support are commercially available.

The DMS cleavage reactions in system 100 are operated such that a mole conversion of DMS to MeSH is greater than about 50%; alternatively, greater than about 60%; alternatively, greater than about 70%; alternatively, greater than about 80%. Conversion is defined as the total number of moles of DMS consumed in the DMS cleavage reactor divided by the total moles of DMS fed to the DMS cleaving reactor, (100*(1-(moles/hr of DMS in the product)/(moles/hr of DMS in the feed))).

The DMS cleavage reactions in system 100 are operated such that a selectivity (on a mole basis) of the catalyst to MeSH is greater than about 95%; alternatively, greater than about 96%; alternatively, greater than about 97%. Selectivity is defined as the total number of moles of MeSH formed divided by the total moles of reaction products formed, (100*(moles/hr of MeSH in the product)/(moles/hr of total reaction products)).

The DMS cleavage reactions in system 100 are operated such that a selectivity of the catalyst to $CS_2$ is less than about 2%; alternatively, less than about 1%; alternatively, less than about 0.5%.

Each reactor 120 or tube reactor 300 can have one or more catalyst beds. Each catalyst bed can include the catalyst in the form of alumina catalyst, NiMo catalyst, CoMo catalyst, or combinations thereof. For example of a combination of catalysts in a single catalyst bed, a NiMo or CoMo catalyst can be diluted (mixed) with alumina catalyst. For catalyst beds of NiMo or CoMo catalyst diluted with alumina catalyst, the mass ratio of NiMo or CoMo catalyst to alumina catalyst can vary between 0:1 to 1:0. In an aspect, the alumina catalyst can be 14-20 mesh (US sieve mesh number) alpha alumina (e.g., an aluminum oxide vitrified product such as ALUNDUM® alumina) spherical particles.

The concentration of the NiMo catalyst or CoMo catalyst across multiple catalyst beds in a single reactor (e.g., in reactor 120 having catalyst beds therein or in each tube reactor 300) can be constant. For example, each catalyst bed can contain only NiMo or CoMo catalyst; alternatively, each catalyst bed can contain the same ratio of NiMo or CoMo catalyst to alumina catalyst. Alternatively, the concentration of the NiMo or CoMo catalyst across multiple catalyst beds in a single reactor (e.g., in reactor 120 having catalyst beds therein or in each tube reactor 300) can vary. For example, the concentration of NiMo or CoMo catalyst across the catalyst beds can decrease, with the catalyst bed which is closest to the reactor inlet (e.g., inlet 121 or inlet 302) including only the NiMo or CoMo catalyst with no dilution by alumina catalyst and with the catalyst bed which is closest to the reactor outlet (e.g., outlet 122 or outlet 304) including only alumina catalyst with no NiMo or CoMo catalyst. In such aspects, any catalyst bed(s) in between the first and last catalyst beds can have any ratio of NiMo or CoMo catalyst to alumina catalyst, and in some aspects, the concentration of NiMo or CoMo catalyst can decrease from bed to bed in the direction of flow while the concentration of the alumina catalyst can increase from bed to bed in the direction of flow.

The reactor effluent stream 110 can receive reactor effluent from the reactor 120. Thus, the reactor effluent stream 110 can contain effluent from the DMS cleavage reactor 120. The composition of the reactor effluent stream 110 is such that mostly $H_2S$ and MeSH are present. As stated herein above, "MeSH" stands for methyl mercaptan, where "Me" is a methyl group ($CH_3$), S is sulfur, and H is hydrogen. As the name "MeSH" indicates, the sulfur atom is bonded to both the methyl group and the hydrogen atom. The chemical formula for methyl mercaptan is $CH_3SH$. In an aspect, the reactor effluent stream 110 is in the vapor phase.

The MeSH can be present in the reactor effluent stream 110 in a range of about 5 wt % to about 25 wt % based on the total weight of all components in the reactor effluent stream 110. Alternatively, the MeSH can be present in the reactor effluent stream 110 in a range of about 10 wt % to about 20 wt % based on the total weight of all components in the reactor effluent stream 110. Alternatively, the MeSH can be present in the reactor effluent stream 110 in a range of about 15 wt % to about 25 wt % based on the total weight of all components in the reactor effluent stream 110. The $H_2S$ can be present in the reactor effluent stream 110 in a range of about 50 wt % to about 80 wt % based on the total weight of all components in the reactor effluent stream 110. Alternatively, the $H_2S$ can be present in the reactor effluent stream 110 in a range of from about 50 wt % to about 75 wt %; alternatively in a range of from about 50 wt % to about 65 wt %. DMS can be present in the reactor effluent stream 110 in a range of less than about 10 wt % based on the total weight of all components in the reactor effluent stream 110; alternatively, in a range of less than about 5 wt %; alternatively in a range of less than about 3 wt %; alternatively in a range of less than about 0.5 wt %; alternatively in a range of less than about 0.05 wt %. Carbon disulfide ($CS_2$) can be present in the reactor effluent stream 110 in a range of less than about 3 wt % based on the total weight of all components in the reactor effluent stream 110; alternatively in a range of less than about 1.5 wt %; alternatively in a range of less than about 0.5 wt %; alternatively in a range of less than about 0.05 wt %. Alternatively, there can be essentially no $CS_2$ present in the reactor effluent stream 110. One or more other components such as $H_2$, methane, $CO_2$, and dimethyl disulfide (DMDS) can be present in the reactor effluent in minor amounts.

Normalized to only the compounds of MeSH, DMS, and $CS_2$, the MeSH can be present in the reactor effluent stream 110 in a range of about 65 wt % to about 75 wt % based on the total weight of MeSH, DMS, and $CS_2$ in the reactor effluent stream 110; alternatively in a range of about 65 wt % to about 70 wt %; alternatively in a range of about 70 wt % to about 65 wt %. DMS can be present in the reactor effluent stream 110 in a range 15 wt % to about 28 wt % based on the total weight of MeSH, DMS, and $CS_2$ in the reactor effluent stream 110; alternatively in a range of about 15 wt % to about 20 wt %; alternatively in a range of from about 20 wt % to about 28 wt %. Carbon disulfide ($CS_2$) can be present in the reactor effluent stream 110 in a range of about 2 wt % to about 10 wt % based on the total weight of MeSH, DMS, and $CS_2$ in the reactor effluent stream 110; alternatively in a range of about 2 wt % to about 5 wt %; alternatively in a range of from about 5 wt % to about 10 wt %.

The MeSH can be present in the reactor effluent stream 110 in a range of about 5 mole % to about 76 mole % based on the total moles of all components in the reactor effluent stream 110. DMS can be present in the reactor effluent stream 110 in a range of about 1 mole % to about 50 mole % based on the total moles of all components in the reactor effluent stream 110. Carbon disulfide ($CS_2$) can be present in the reactor effluent stream 110 in a range of less than about 2 mole %, alternatively, less than about 1 mole %, alternatively, less than about 0.5 mole % based on the total moles of all components in the reactor effluent stream 110. DMDS can be present in the reactor effluent stream 110 in a range of less than about 0.5 mole % based on the total moles of all components in the reactor effluent stream 110.

Normalized to only the compounds of MeSH, DMS, and $CS_2$, the MeSH can be present in the reactor effluent stream 110 in a range of about 50 mole % to about 73 mole % based on the total moles of MeSH, DMS, and $CS_2$ in the reactor effluent stream 110. DMS can be present in the reactor effluent stream 110 in a range of about 19 mole % to about 50 mole % based on the total moles of MeSH, DMS, and $CS_2$ in the reactor effluent stream 110. Carbon disulfide ($CS_2$) can be present in the reactor effluent stream 110 in a range of about 1.5 mole % to about 8 mole % based on the total moles of MeSH, DMS, and $CS_2$ in the reactor effluent stream 110.

In an aspect, the reactor effluent stream 110 flows to the preheater 130, where the reactor effluent exchanges heat with the combined feed in combined feed stream 106 and is cooled to form the cooled reactor effluent in cooled reactor effluent stream 112. In an aspect the reactor effluent can exchange heat with a cooling medium other than the combined feed (e.g., cooling water or the contents of another process stream). As discussed above, the cooled effluent can flow in the cooled reactor effluent stream 112 for further processing (see FIG. 2) or for recycle to a methyl mercaptan production plant (see FIG. 3). The composition of the cooled reactor effluent stream 112 can be the same as the reactor effluent stream 110, with the ranges and composition values being based on a total moles or weight in the cooled reactor effluent stream 112. In an aspect, the cooled reactor effluent is in the vapor phase, the liquid phase, a mixture of vapor and liquid phases, or the cooled reactor effluent can be in the vapor phase in one portion of stream 112 and in the liquid phase in another portion of stream 112.

Figure 2:
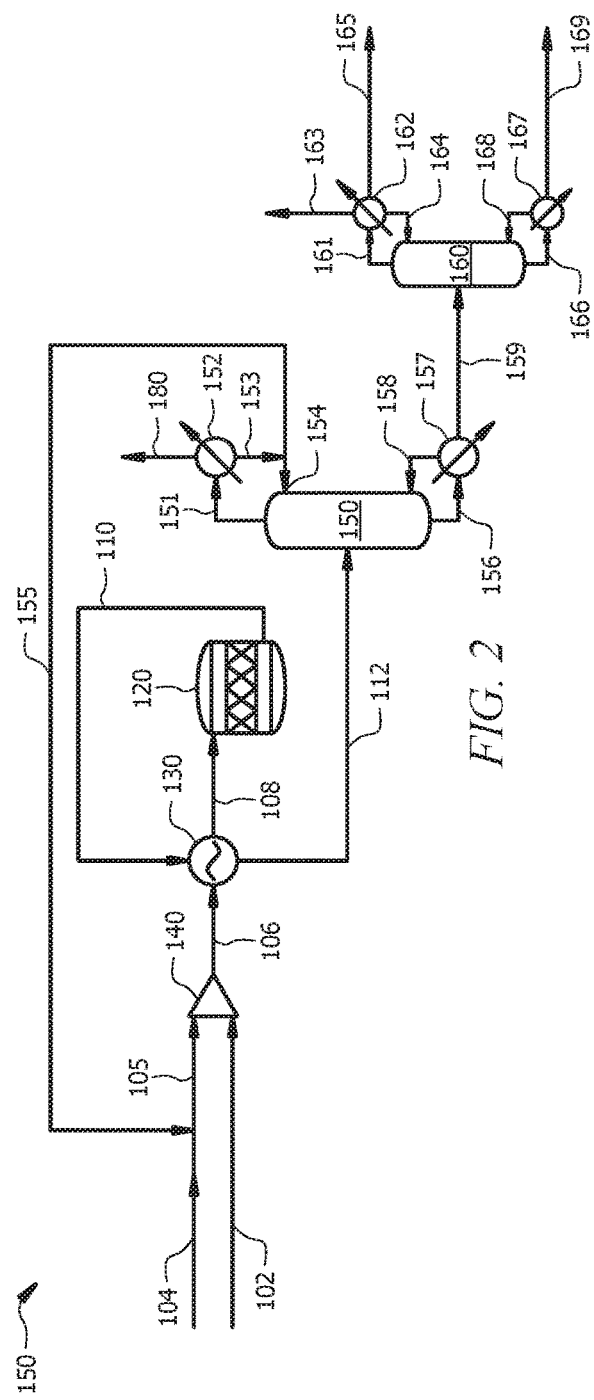
FIG. 2 illustrates a standalone system which utilizes the system and numerical nomenclature of FIG. 1 and incorporates further processing of the cleavage reactor effluent.

FIG. 2 illustrates a standalone system 150 which utilizes the system 100 for converting dimethyl sulfide to methyl mercaptan. The system 150 in FIG. 2 can also be referred to herein as a "DMS cleavage system" and any processes performed using the system 150 can be referred to herein as a "DMS cleavage process." The system 150 of FIG. 2 provides an example of further processing of the cooled reactor effluent stream 112 via use of separators 150 and 160, while incorporating $H_2S$ recycle to the DMS cleavage reactor 120 via stream 155.

The DMS cleavage system 150 in FIG. 2 can include one or more of a DMS stream 102, a $H_2S$ stream 104, a combined $H_2S$ stream 105 (combination of the $H_2S$ stream 104 and a recycle $H_2S$ stream 155), a mixing device 140, a combined feed stream 106, a preheater 130, a heated feed stream 108, a reactor 120, a reactor effluent stream 110, a cooled effluent stream 112, a separator 150, and another separator 160. Associated with the separator 150 is one or more of an overhead stream 151, a cooler (e.g., condenser) 152, a cooled overhead stream 153, a vent stream 180, a reflux stream 154, a recycle $H_2S$ stream 155, a bottoms stream 156, a reboiler 157, a reboiler effluent stream 158, and a heated bottoms stream 159. Associated with the other separator 160 is one or more of an overhead stream 161, a cooler (e.g., condenser) 162, a vent stream 163, a reflux stream 164, a MeSH product stream 165, a bottoms stream 166, a reboiler 167, a reboiler effluent stream 168, and a liquid waste stream 169.

The $H_2S$ stream 104 and the recycle $H_2S$ stream 155 can combine to form the combined $H_2S$ stream 105. The DMS stream 102 and the combined $H_2S$ stream 105 can be mixed in the mixing device 140 to form the combined feed stream 106 containing the contents of both the DMS stream 102 and the combined $H_2S$ stream 105.

The hydrogen sulfide and dimethyl sulfide can be fed to the reactor 120 via the combined feed stream 106. For example, the combined feed stream 106 can be heated in a preheater 130 to the temperature of the DMS cleavage reaction in the reactor 120. The heated feed stream 108 can flow from the preheater 130 to the reactor 120, where at least some of the DMS can be converted to MeSH under DMS cleavage reaction conditions in the presence of a catalyst described hereinbelow. Reactor effluent can flow from the reactor 120 in reactor effluent stream 110 to the preheater 130, where the reactor effluent can be cooled. The cooled effluent can flow in the cooled reactor effluent stream 112 to the separator 150.

As described for FIG. 1, the cooled reactor effluent stream 112 can contain large amounts of $H_2S$ (in a range of about 50 wt % to about 80 wt % based on the total weight of all components in the cooled reactor effluent stream 112). This can also apply to the reactor effluent stream 112 of FIG. 2. Thus, process steps in FIG. 2 can include separating the reactor effluent into a recycle $H_2S$ stream 155 and a methyl mercaptan stream 159, and recycling the recycle $H_2S$ stream 155 for use in the step of contacting which occurs in the reactor 120.

In the separator 150, $H_2S$ can separate from the other components received from the cooled reactor effluent stream 112. Most of the $H_2S$ can be recovered in the overhead stream 151, and the remaining components, e.g., MeSH, DMS, $CS_2$, or a combination thereof can flow from the separator 150 in the bottoms stream 156.

The overhead stream 151 can be cooled in the cooler (e.g., condenser) 152 to form a cooled overhead stream 153 containing cooled $H_2S$. Uncondensed light components can be vented from the system 150 in vent stream 180. A portion of the cooled overhead stream can flow back to a top portion of the separator 150 in reflux stream 154, and another portion (or all) of the cooled overhead stream can recycle $H_2S$ in recycle $H_2S$ stream 155 to combine with $H_2S$ stream 104. The recycle $H_2S$ stream 155 can include mostly $H_2S$ and less than about 5 mole %, alternatively, less than about 2 mole %, alternatively, less than about 1 mole % MeSH.

The bottoms stream 156 can be heated in a reboiler 157. A reboiler effluent stream 158 can flow a portion of the heated bottoms back to a bottom portion of the separator 150 in reboiler effluent stream 158. Another portion (or all) of the heated bottoms can flow in methyl mercaptan stream 159 to another (a second) separator 160.

The other separator 160 (also referred to as the second separator) receives the heated bottoms from stream 159 and separates the components (e.g., MeSH and one or more of DMS and $CS_2$) into an overhead stream 161 containing MeSH and a bottoms stream 166 containing liquid waste (e.g., DMS, DMDS, and $CS_2$). The overhead stream 161 can be cooled in cooler 162. In an aspect, the cooler 162 can be a condenser which can condense MeSH from the vapor phase to the liquid phase. The cooler 162 can also include a separation vessel (e.g., an accumulator) so as to separate the vapor from the liquid. For example, the vapor can contain any light components which are received from the bottoms stream 159 by the second separator 160, and the light components can be vented from the system 150 in vent stream 163. The liquid can include MeSH product containing MeSH of a high purity (e.g., greater than 95, 96, 97, 98, or 99 wt % based on the total weight of stream 164 or stream 165). The MeSH product can be divided such that a first portion can flow back to the second separator 160 in reflux stream 164, and a second portion (or all) can flow in stream 165 for further use.

The reactor 120, preheater 130, and mixing device 140 in system 150 can have the same configurations as described for system 100. The total flow of $H_2S$ in stream 104 can be reduced as compared to the flow in the corresponding stream 104 of FIG. 1 such that upon combination of the $H_2S$ stream 104 with the recycle $H_2S$ stream 155, the flow of $H_2S$ in combined $H_2S$ stream 105 and the flow of DMS in DMS stream 102 can provide $H_2S$ in excess (e.g., a mole ratio of $H_2S$ to DMS ($H_2S$:DMS) of at least 3:1, alternatively at least 5:1; alternatively, at least 10:1; additionally or alternatively, less than 100:1) in the combined feed stream 106, the heated feed stream 108, and/or the reactor 120.

Separator 150 and separator 160 can be any separator suitable for separating MeSH from the other components in the cooled reactor effluent. For example, separator 150 and separator 160 can each be a distillation column or fractionation column. Each column can be a vessel having internal components such as distillation trays (for example sieve-type, dual-flow, bubble cap, donut), packing materials, or both.

The coolers (e.g., condensers) 152 and 162 can be any heat exchanger which can cool (heat is transferred out of the overhead streams 151 and 161) by exchanging thermal energy with a cooling medium (e.g., cooling water or refrigerant). The coolers 152 and 162 can have any configuration to cool the overhead streams 151 and 161. The reboilers 157 and 167 can be any heat exchanger known which can heat (heat is transferred into the bottoms streams 156 and 166) by exchanging thermal energy with a heating medium or by direct heat. The reboilers 157 and 167 can have any configuration to heat the bottoms streams 156 and 166.

Figure 3:
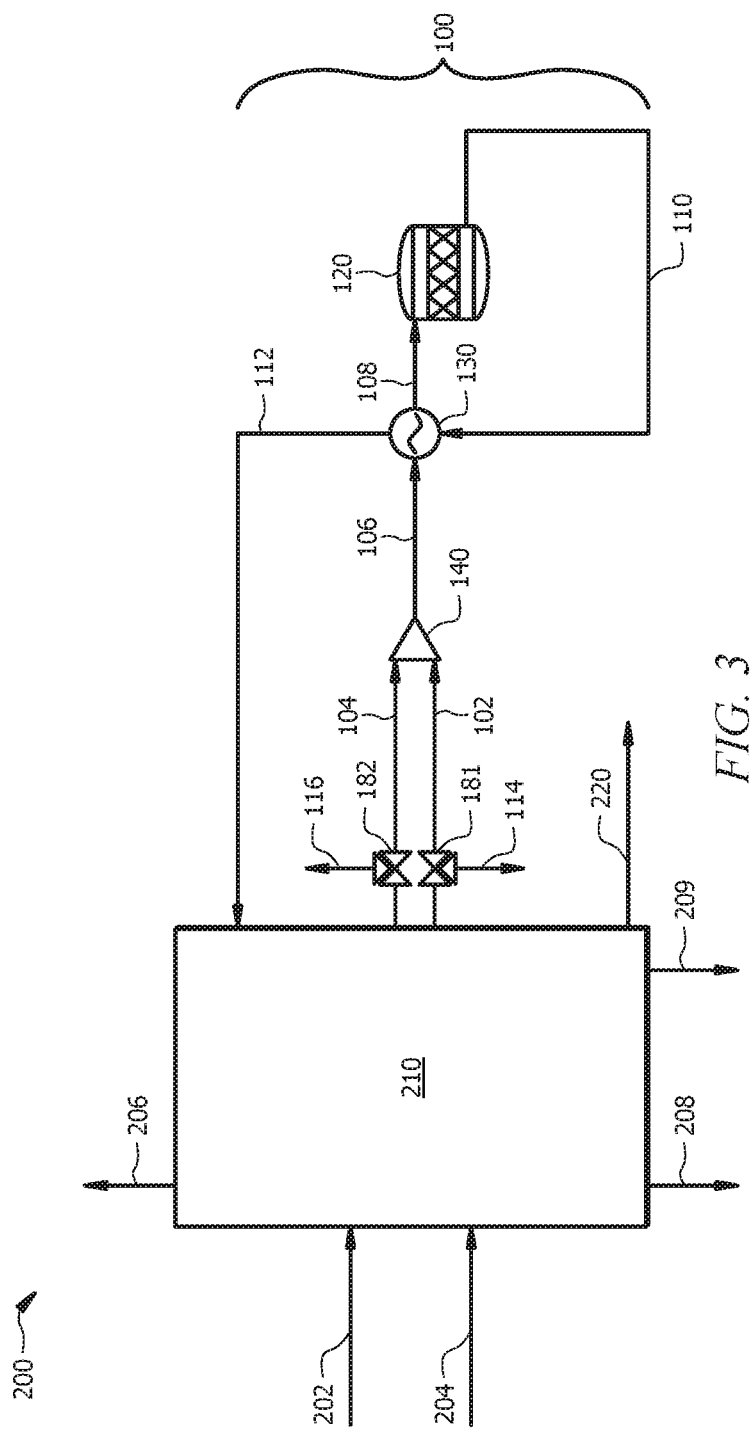
FIG. 3 illustrates an integrated system which utilizes the system and numerical nomenclature of FIG. 1 in combination with a methyl mercaptan production plant, where the cleavage reactor effluent recycles to the methyl mercaptan production plant.

FIG. 3 illustrates an integrated system 200 which utilizes the system 100 in combination with a methyl mercaptan production plant 210. The system 200 in FIG. 3 can be referred to herein as an "integrated DMS cleavage system" and any processes performed using the system 200 can be referred to herein as an "integrated DMS cleavage process."

The methyl mercaptan production plant 210 can be any plant having a reactor (also referred to herein as a "MeSH reactor") which catalytically produces a methyl mercaptan product, for example, according to the following reaction:

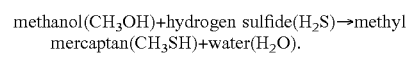

$$\text{methanol}(CH_3OH) + \text{hydrogen sulfide}(H_2S) \rightarrow \text{methyl mercaptan}(CH_3SH) + \text{water}(H_2O).$$

Nonlimiting examples of methyl mercaptan production plant 210 are described in U.S. Pat. Nos. 2,822,400 and 3,792,094. In the MeSH reactor, methanol and hydrogen sulfide can be contacted in presence of a catalyst under conditions suitable to yield a reactor effluent (also referred to herein as "MeSH reactor effluent"). Depending on the purity of the $H_2S$ feed stream 202 and methanol feed stream 204, as well as reaction conditions, the MeSH reactor effluent of the MeSH reactor in the plant 210 can include the desired methyl mercaptan and other compounds which can include but are not limited to methanol (MeOH), hydrogen sulfide ($H_2S$), hydrogen ($H_2$), carbon monoxide (CO), carbon dioxide ($CO_2$), light hydrocarbons, dimethyl sulfide (DMS), dimethyl disulfide (DMDS), water ($H_2O$), mercaptans higher than MeSH, or combinations thereof.

The methyl mercaptan production plant 210 can also include various separation stages known in the art and with the aid of this disclosure for isolating and recovering the methyl mercaptan from any of the above mentioned compounds in the reactor effluent, as well as separation techniques for isolating and recovering any of the compounds from one another. For example, one or more of the separation stages in the methyl mercaptan production plant 210 can recover at least a portion of the dimethyl sulfide from the MeSH reactor effluent to yield recovered DMS in the DMS stream 102. One or more of the separation stages in the methyl mercaptan production plant 210 can also recover at least a portion of the $H_2S$ from the MeSH reactor effluent to yield recovered $H_2S$ in the $H_2S$ stream 104. One or more of the separation stages in the methyl mercaptan production plant 210 can also recover at least a portion of the MeSH product from the MeSH reactor effluent to yield recovered MeSH product in the MeSH product stream 220.

As a result of various separation stages, the methyl mercaptan production plant 210 illustrated in FIG. 3 can output the DMS stream 102 which flows to the DMS cleavage reactor 120, the $H_2S$ stream 104 which flows to the DMS cleavage reactor 120, one or more vent streams collectively shown by vent purge stream 206, an organic liquid purge stream 208, an aqueous purge stream 209, and a MeSH product stream 220.

The DMS cleavage system 100 can operate in the same manner and under the same conditions as described for FIG. 1. In the integrated system 200, all or a portion of the cooled reactor effluent stream 112 from the DMS cleavage system 100 can recycle cooled reactor effluent in cooled reactor effluent stream 112 back to the methyl mercaptan production plant 210 to a location in or downstream of the MeSH reactor effluent and upstream of a step or stage for separating $H_2S$ from the MeSH contained in the cooled effluent stream 112. For example, the cooled reactor effluent stream 112 can recycle to and combine with the MeSH reactor effluent before any separation steps or stages in the methyl mercaptan production plant 210. Alternatively, the cooled reactor effluent stream 112 can recycle to and i) combine with an intermediate separation stream or ii) feed to an intermediate separator, which is downstream of the MeSH reactor effluent. In an aspect, the intermediate stream can be a stream which flows MeSH product between two separation stages/ steps which ultimately can recover the MeSH product in the MeSH product stream 220 or which are included in a plurality of separation stages which ultimately recover the MeSH product in the MeSH product stream 220.

In an aspect, the DMS stream 102 and the $H_2S$ stream 104 can include appropriate equipment to control the flow of $H_2S$ and DMS to the DMS cleavage system 100. Controlling the flow of $H_2S$ and DMS from the plant 210 to the system 100 allows for the integrated system 200 to adjustably convert DMS to MeSH under a first set of market conditions, and likewise, to cease converting DMS to MeSH under a second set of market conditions. By way of example only, a valve 181 (shown in FIG. 3 as a 3-way valve) can be included in DMS stream 102, and a valve 182 (shown in FIG. 3 as a 3-way valve) can be included in the $H_2S$ stream 104. In a first position, valve 181 can allow DMS to flow in the DMS stream 102 to the mixer 140 and on to the DMS cleavage reactor 120. In a second position, valve 181 can discontinue the flow of DMS to the reactor 120 and instead allow DMS to flow in DMS product stream 114. The DMS product stream 114 can flow DMS for storage, or for further processing which recovers DMS according to known methods to a purity suitable for sale or use in other processes. In a first position, valve 182 can allow $H_2S$ to flow in the $H_2S$ stream 104 to the DMS cleavage reactor 120. In a second position, valve 182 can discontinue the flow of $H_2S$ to the reactor 120 and instead allow $H_2S$ to flow in a second $H_2S$ stream 116. $H_2S$ in the second $H_2S$ stream 116 can flow back to the plant 210 for use therein, for example, in the MeSH reactor. It is contemplated that the integrated system 200 can operate: i) with valve 181 in the first position and valve 182 in the first position so as to flow both $H_2S$ and DMS to the reactor 120; ii) with valve 181 in the second position and valve 182 in the second position so as to flow DMS in stream 114 for subsequent processing or storage and to flow $H_2S$ in stream 116 back to the plant 210; iii) with valve 181 in the first position so that all of the DMS flows to the reactor 120 and valve 182 in the second position so that a portion of the $H_2S$ flows in stream 116; or iv) valve 181 in the second position so that a portion of the DMS flows to stream 114 and valve 182 in the first position so that all of the $H_2S$ flows to the reactor 120.

The integrated system 200 can provide a MeSH product stream 220 having MeSH present in an amount of greater than 0.900, 0.950, 0.990, 0.991, 0.992, 0.993, 0.994, 0.995, 0.996, 0.997, 0.998 mole fraction based on the total moles of components in the MeSH product stream 220. The MeSH product stream 220 can also have less than about 50 ppmw $CS_2$ based on the total weight of the MeSH product stream; alternatively less than about 30 ppmw $CS_2$ based on the total weight of the MeSH product stream; alternatively less than about 20 ppmw $CS_2$ based on the total weight of the MeSH product stream; alternatively less than about 10 ppmw $CS_2$ based on the total weight of the MeSH product stream; alternatively less than about 5 ppmw $CS_2$ based on a total weight of the MeSH product stream 220. In an embodiment, the MeSH product stream contains essentially no $CS_2$. One or more of DMS, dimethyl disulfide (DMDS), $CS_2$ and components heavier than MeSH can be recovered in the organic liquid purge stream 208. The organic liquid purge stream 208 can have less than about 20 ppmw $CS_2$ based on the total weight of the organic liquid purge stream 208. Water can be recovered in the aqueous purge stream 209. One or more of hydrogen, nitrogen, methane, $CO_2$, $H_2S$, MeSH, DMS, and methanol can be recovered in the vent purge stream 206.

The vent purge stream 206, the organic liquid purge stream 208, the aqueous purge stream 209, and any other purge stream recovered from the methyl mercaptan production plant 210 can be individually and collectively referred to herein as "one or more purge streams." One or more of these purge streams (e.g., one or more of the vent purge stream 206, the organic liquid purge stream 208, the aqueous purge stream 209, and any other purge stream recovered from the methyl mercaptan production plant 210) can include dimethyl sulfide in an amount which is less than about 5 wt % based on the weight of dimethyl sulfide in the DMS stream 102 (e.g., the weight of dimethyl sulfide fed to the DMS cleavage reactor 120). When recovering one or more of these purge streams from the methyl mercaptan production plant 210, the purge streams can collectively comprise equal to or less than about 10 mole % carbon disulfide based on a total moles in the purge streams.

Figure 4:
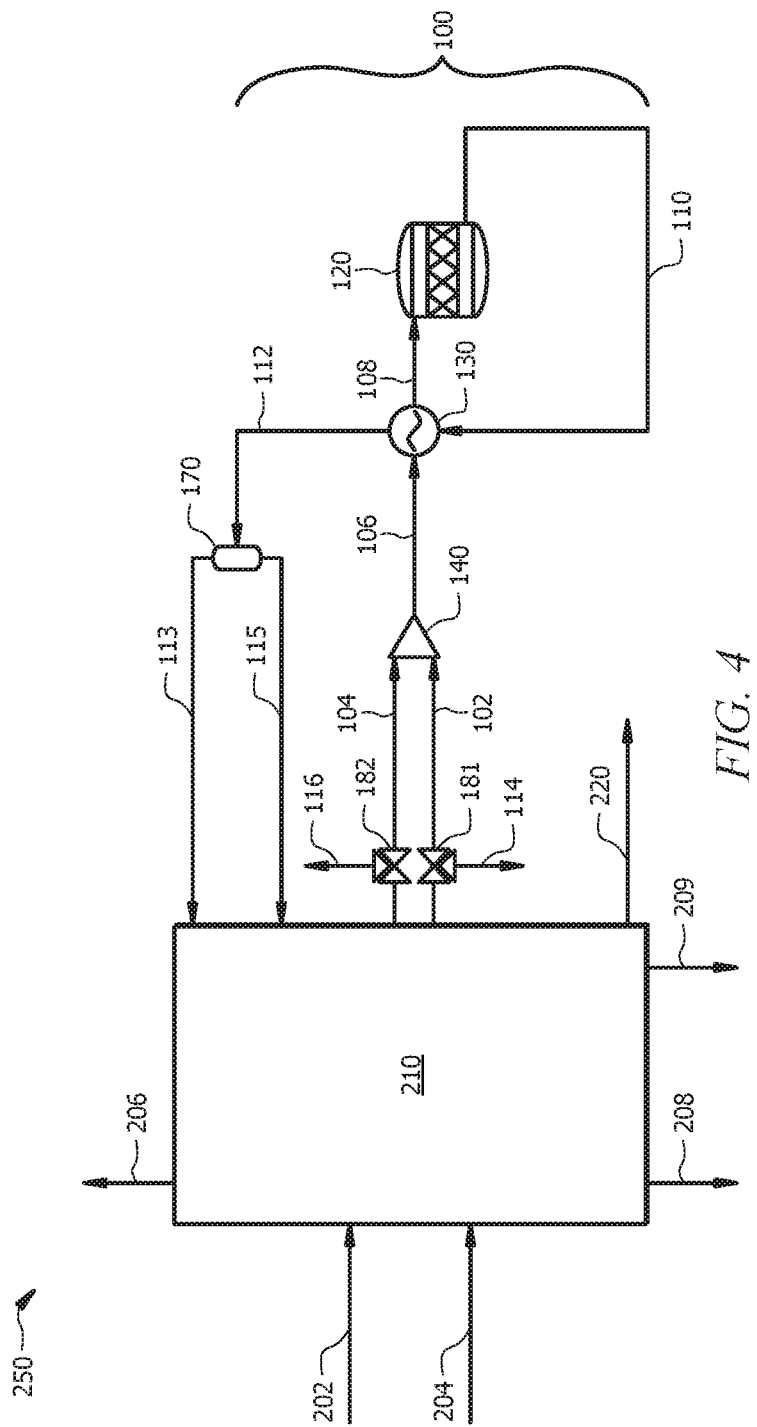
FIG. 4 illustrates an integrated system which utilizes the system and numerical nomenclature of FIGS. 1 and 3 in combination with a methyl mercaptan production plant, where the cleavage reactor effluent is separated before the methyl mercaptan is recycled to the methyl mercaptan production plant.

FIG. 4 illustrates an integrated system 250 which utilizes the system 100 of FIG. 1 in combination with a methyl mercaptan production plant 210, where the cooled reactor effluent stream 112 is separated before the methyl mercaptan and $H_2S$ from stream 112 are recycled to the methyl mercaptan production plant 210. FIG. 4 also illustrates vent gases are removed from the plant 210 in one or more vent streams collectively shown by vent purge stream 206.

The DMS cleavage system 100 can operate in the same manner and under the same conditions as described for FIG. 1. Suitable equipment to control the flow of DMS and $H_2S$ to the reactor 120 can likewise be utilized in the system 250 of FIG. 4 (e.g., valves 181 and 182 and streams 114 and 116), in the same manner as described for system 200 in FIG. 3.

As can be seen in FIG. 4, the cooled reactor effluent stream 112 of the system 250 can flow all or a portion of the cooled DMS reactor effluent to a separation vessel 170 (e.g., a flash tank, or a distillation column such a separator 150 in FIG. 2), which can separate $H_2S$ from the other components (e.g., MeSH) of stream 112 to produce an enriched $H_2S$ stream 113 flowing overhead and an enriched MeSH stream 115 flowing from the bottom of the separation vessel 170.

The enriched $H_2S$ stream 113 can flow or recycle $H_2S$ (e.g., and optionally other light components such as hydrogen, methane, and carbon dioxide which flash in the separation vessel 170) to the methyl mercaptan production plant 210, for example, to a location upstream of the separation stage or step of the plant 210 which recovers $H_2S$ from any component described herein. The enriched MeSH stream 115 can flow or recycle the remaining components (e.g., including MeSH and one or both of DMS and $CS_2$) to the methyl mercaptan production plant 210, for example, to a location in the separation stages/steps of the plant 210 upstream of where such components are separated. In FIG. 4, the methyl mercaptan in enriched MeSH stream 115 can be recycled to the plant 210 separately of the $H_2S$ in the enriched $H_2S$ stream 113.

In an aspect where the separation vessel 170 is a vapor/liquid separator such as a flash tank, it is contemplated that the cooled reactor effluent stream 112, which can be in a vapor phase, can be cooled to a temperature in which components heavier than $H_2S$ (e.g., MeSH and one or both of DMS and $CS_2$) condense to a liquid such that $H_2S$ separates as a vapor from the MeSH in vapor/liquid separator. In such as aspect, the enriched $H_2S$ stream 113 can be in the vapor phase, and the enriched MeSH stream 115 can be in a liquid phase. Additional heat exchangers (e.g., condensers) can be included in the cooled reactor effluent stream 112 to effect the vapor/liquid separation in the separation vessel 170.

The integrated system 250, similar to integrated system 200, can provide a MeSH product stream 220 having less than about 5 ppmw $CS_2$ based on a total weight of the MeSH product stream 220. One or more of DMS, dimethyl disulfide (DMDS), $CS_2$ and components heavier than MeSH can be recovered in the organic liquid purge stream 208. Water can be recovered in the aqueous purge stream 209. One or more of hydrogen, nitrogen, methane, $CO_2$, MeSH, DMS, and methanol can be recovered in the vent purge stream 206.

FIG. 5 illustrates a DMS cleavage reactor in the form of a tube reactor 300. The tube reactor 300 is discussed in detail above and in the examples below, and as such, discussion is not reproduced here.

The disclosed systems and processes can allow for the catalyzed cleavage of DMS to produce MeSH by using already-existing streams from a methyl mercaptan production plant, such as plant 210 disclosed herein. In converting DMS to MeSH, the amount of DMS present can be decreased and the amount of MeSH present can be increased in integrated systems 200 and 250. On the other hand, the flow of $H_2S$ and DMS in the systems and processes disclosed herein can be adjusted so that conversion of DMS to MeSH is discontinued, and so that DMS can be recovered for other uses or processing. In general, the systems and processes can readily be adjusted between a state which utilizes the DMS cleavage system 100 and a second state which does not utilize the DMS cleavage system 100.

The disclosed systems and processes allow for production flexibility between DMS and MeSH according to market conditions. That is, during certain market conditions, for example, when the price difference between DMS and MeSH justifies converting DMS to MeSH, the lower value DMS can be converted to higher value MeSH. In some aspects, the amount of DMS in the market can cause oversupply, and the market price of DMS can drop to unprofitable levels. The ability of the disclosed systems and processes to utilize DMS conversion to MeSH in such market conditions can reduce if not eliminate losses associated with continued DMS production at variable or unprofitable market conditions.

Thus, a contemplated process according to the disclosure includes utilizing a methyl mercaptan production plant to recover dimethyl sulfide, responsive to a first market condition, contacting at least a portion of the recovered dimethyl sulfide with a CoMo or NiMo catalyst in the presence of hydrogen sulfide in a reactor to yield a reactor effluent comprising methyl mercaptan, hydrogen sulfide, and carbon disulfide, responsive to a second market condition, discontinuing the contacting of the recovered dimethyl sulfide in the reactor, and selling all or a portion of the recovered dimethyl sulfide. The first market condition can be that the market value (e.g., manufacturer's price) of dimethyl sulfide falls below a profitable level or that the market value (e.g., manufacturer's price) of dimethyl sulfide is less than the market value (e.g., manufacturer's price) of MeSH. The second market condition can be that the market value (e.g., manufacturer's price) of dimethyl sulfide rises above an uprofitable level and/or the market is undersupplied with DMS.

Another process can include contacting at least a portion of the recovered dimethyl sulfide with a CoMo or NiMo catalyst in the presence of hydrogen sulfide in a reactor to yield a reactor effluent comprising methyl mercaptan, hydrogen sulfide, and carbon disulfide, wherein the recovered dimethyl sulfide is obtained from a methyl mercaptan production plant, responsive to a first market condition, discontinuing the contacting of the recovered dimethyl sulfide in the reactor, selling all or a portion of the recovered dimethyl sulfide, and responsive to a second market condition, repeating the step of contacting. The first market condition in such an aspect can be that the market value (e.g., manufacturer's price) of dimethyl sulfide rises above an unprofitable level and/or the market is undersupplied with DMS. The second market condition in such an aspect can be that the market value (e.g., manufacturer's price) of dimethyl sulfide falls below a profitable level or that the market value (e.g., manufacturer's price) of dimethyl sulfide is less than the market value (e.g., manufacturer's price) of MeSH.

The disclosed systems and processes also can provide for a higher MeSH production rate in the methyl mercaptan production plant 210 because MeSH produced by DMS conversion in the DMS cleavage system 100 can be recycled to the plant 210, which increases the flow of MeSH recovered from the plant 210. Further, the MeSH product which can be produced in the integrated systems 200 and 250 according to the processes disclosed herein has a MeSH product having on-spec $CS_2$ requirements.

The disclosed systems and processes also allow the DMS cleavage system 100 to utilize existing separation stages and/or steps in a methyl mercaptan production plant 210 instead of requiring capital investment in a MeSH separation train dedicated only to the DMS cleavage reactor 120. Utilization of existing separation stages and/or step in the methyl mercaptan production plant 210 can lower capital cost associated with building the DMS cleavage system 100 or 150.

The disclosed systems and processes also allow for recovery of merchant DMS (DMS for sale) from a methyl mercaptan production plant via a DMS purge stream, for example, the organic liquid purge stream 208 in FIG. 3 and FIG. 4. Carbon disulfide, once formed, is not converted in the DMS cleavage reactor 120, and the DMS cleavage reactor 120 can also produce carbon disulfide; thus, the unconverted (and optionally produced) carbon disulfide can flow in the DMS cleavage reactor effluent stream 110. To obtain the disclosed purity of MeSH product from the methyl mercaptan production plant 210, the carbon disulfide can be recovered in other streams in the methyl mercaptan production plant 210, for example, stream 208. The value of merchant DMS (e.g., in stream 208) depends upon its purity, which can be processed to reduce the amount of carbon disulfide to a buyer's desired level. The disclosed integrated systems and processes thus allow for recovery of merchant DMS from the methyl mercaptan production plant 210, for example, via organic liquid purge stream 208.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

In Example 1, runs were conducted for a standalone DMS cleavage system and process. A stainless steel reactor having a diameter of 1 inch (2.54 cm) was used. The catalyst used in Example 1 was a 3% Co, 10% Mo, alumina supported catalyst. The catalyst was in the form of 0.05 inch (1.27 mm) extrudates. The catalyst was diluted with 14-20 mesh alpha alumina (ALUNDUM® alumina) spherical particles, and this diluted combination of catalyst and 14-20 mesh alpha alumina was used as the catalyst bed. Reactor heating was provided by an external electric furnace having three heating zones. Temperatures were measured and controlled using thermocouples in a thermowell inserted axially through the center of the catalyst bed. The pressure for all the runs in Example 1 was 450 psig (3103 kPa).

A DMS stream and a $H_2S$ stream were connected to the reactor. Before flowing into the reactor, the DMS in the DMS stream was dried by passing it over type 3A molecular sieve beads.

Data for Runs 1 to 62 is shown below, at various weight hourly space velocities (WHSV) defined by gram of DMS per gram of catalyst per hour (g DMS/g cat./h), $H_2S$:DMS mole ratios, and temperatures. WHSV was varied from 0.25 to 2.0. The $H_2S$:DMS mole ratio was 3, 6, or 9. Temperature was varied between 200° C. and 350° C. in increments of 25° C.

TABLE 1

Standalone DMS Cleavage Process Run Data

| | WHSV | | | Reactor Effluent | | | | | | |
|---|---|---|---|---|---|---|---|---|---|---|
| Run | g DMS/g cat./h | $H_2S$:DMS Mole Ratio | Temp. ° C. | MeSH Mole % | DMS Mole % | $CS_2$ Mole % | DMDS Mole % | DMS Conv. | MeSH Select. | $CS_2$ Select. |
| 1 | 0.25 | 3 | 200 | 14.0% | 84.4% | 0.2% | 0.0% | 8.4% | 90.2% | 1.2% |
| 2 | 0.25 | 3 | 225 | 37.1% | 61.3% | 0.2% | 0.0% | 24.0% | 95.8% | 0.5% |
| 3 | 0.25 | 3 | 250 | 59.1% | 39.3% | 0.2% | 0.3% | 43.7% | 97.7% | 0.2% |
| 4 | 0.25 | 3 | 275 | 59.8% | 38.5% | 0.2% | 0.3% | 44.5% | 97.8% | 0.3% |
| 5 | 0.25 | 3 | 300 | 60.2% | 36.6% | 1.6% | 0.4% | 46.6% | 95.4% | 2.5% |
| 6 | 0.25 | 3 | 325 | 64.4% | 34.3% | 1.7% | 0.2% | 49.7% | 95.6% | 2.6% |
| 7 | 0.25 | 3 | 350 | 54.2% | 15.1% | 26.1% | 0.3% | 73.9% | 64.0% | 30.8% |
| 8 | 1.0 | 3 | 200 | 43.3% | 54.9% | 0.0% | 0.3% | 29.3% | 96.7% | 0.0% |
| 9 | 1.0 | 3 | 225 | 55.5% | 42.5% | 0.5% | 0.4% | 40.5% | 97.1% | 0.8% |
| 10 | 1.0 | 3 | 250 | 57.0% | 40.0% | 1.3% | 0.4% | 43.0% | 95.7% | 2.1% |
| 11 | 1.0 | 3 | 275 | 58.2% | 39.6% | 0.7% | 0.3% | 43.3% | 96.9% | 1.2% |
| 12 | 1.0 | 3 | 300 | 59.9% | 37.5% | 1.0% | 0.2% | 45.5% | 96.3% | 1.5% |
| 13 | 1.0 | 3 | 325 | 60.0% | 36.0% | 2.0% | 0.3% | 47.2% | 94.2% | 3.1% |
| 14 | 1.0 | 3 | 350 | 60.8% | 31.9% | 4.5% | 0.3% | 51.7% | 89.6% | 6.7% |
| 15 | 2.0 | 3 | 200 | 33.6% | 63.7% | 0.2% | 0.2% | 22.3% | 93.1% | 0.6% |
| 16 | 2.0 | 3 | 225 | 55.4% | 42.3% | 0.4% | 0.3% | 40.7% | 96.5% | 0.8% |
| 17 | 2.0 | 3 | 250 | 58.4% | 39.1% | 1.0% | 0.4% | 44.0% | 96.4% | 1.6% |
| 18 | 2.0 | 3 | 275 | 60.1% | 37.9% | 0.6% | 0.2% | 45.1% | 97.0% | 1.0% |
| 19 | 2.0 | 3 | 300 | 60.5% | 37.3% | 0.8% | 0.2% | 45.7% | 96.8% | 1.3% |
| 20 | 2.0 | 3 | 325 | 60.1% | 37.1% | 1.3% | 0.2% | 46.0% | 95.8% | 2.1% |
| 21 | 2.0 | 3 | 350 | 58.3% | 35.5% | 3.6% | 0.2% | 47.8% | 90.7% | 5.6% |
| 22 | 0.25 | 6 | 200 | 61.3% | 36.7% | 0.3% | 0.3% | 46.4% | 97.3% | 0.4% |
| 23 | 0.25 | 6 | 225 | 64.4% | 33.4% | 0.6% | 0.3% | 50.1% | 97.0% | 0.9% |
| 24 | 0.25 | 6 | 250 | 65.5% | 31.9% | 0.8% | 0.3% | 51.8% | 96.6% | 1.2% |
| 25 | 0.25 | 6 | 275 | 67.1% | 30.4% | 0.9% | 0.2% | 53.5% | 96.6% | 1.3% |
| 26 | 0.25 | 6 | 300 | 68.0% | 28.5% | 1.5% | 0.2% | 55.7% | 95.5% | 2.1% |
| 27 | 0.25 | 6 | 325 | 68.4% | 24.5% | 4.3% | 0.2% | 60.8% | 90.9% | 5.7% |
| 28 | 0.25 | 6 | 350 | 64.2% | 16.3% | 14.8% | 0.3% | 72.0% | 77.0% | 17.7% |
| 29 | 1.0 | 6 | 200 | 44.9% | 52.7% | 0.3% | 0.3% | 31.1% | 95.5% | 0.6% |
| 30 | 1.0 | 6 | 225 | 63.2% | 34.3% | 0.6% | 0.3% | 49.0% | 96.8% | 0.8% |
| 31 | 1.0 | 6 | 250 | 65.6% | 31.6% | 0.7% | 0.4% | 52.1% | 96.5% | 1.1% |
| 32 | 1.0 | 6 | 275 | 68.3% | 29.1% | 0.7% | 0.3% | 55.1% | 96.7% | 1.0% |
| 33 | 1.0 | 6 | 300 | 68.2% | 28.1% | 0.9% | 0.0% | 56.2% | 94.9% | 1.3% |
| 34 | 1.0 | 6 | 325 | 69.8% | 26.7% | 1.7% | 0.0% | 57.9% | 95.1% | 2.4% |
| 35 | 1.0 | 6 | 350 | 70.0% | 23.8% | 3.5% | 0.0% | 61.5% | 91.8% | 4.6% |
| 36 | 1.5 | 6 | 200 | 36.1% | 61.2% | 0.3% | 0.3% | 24.2% | 93.4% | 0.8% |
| 37 | 1.5 | 6 | 225 | 61.7% | 35.8% | 0.4% | 0.3% | 47.5% | 96.5% | 0.6% |
| 38 | 1.5 | 6 | 250 | 68.0% | 29.0% | 0.6% | 0.3% | 54.9% | 97.3% | 0.9% |
| 39 | 1.5 | 6 | 275 | 66.4% | 28.2% | 0.8% | 0.0% | 56.0% | 92.5% | 1.1% |
| 40 | 1.5 | 6 | 300 | 69.3% | 27.9% | 1.0% | 0.0% | 56.4% | 96.0% | 1.4% |
| 41 | 1.5 | 6 | 325 | 70.0% | 26.7% | 1.6% | 0.0% | 57.9% | 95.5% | 2.2% |
| 42 | 1.5 | 6 | 350 | 69.6% | 24.0% | 3.6% | 0.0% | 61.4% | 91.5% | 4.7% |

TABLE 1-continued

Standalone DMS Cleavage Process Run Data

| | WHSV | | | Reactor Effluent | | | | | | |
|---|---|---|---|---|---|---|---|---|---|---|
| Run | g DMS/g cat./h | H$_2$S:DMS Mole Ratio | Temp. °C. | MeSH Mole % | DMS Mole % | CS$_2$ Mole % | DMDS Mole % | DMS Conv. | MeSH Select. | CS$_2$ Select. |
| 43 | 0.25 | 9 | 200 | 13.6% | 83.8% | 0.9% | 0.0% | 8.8% | 84.0% | 5.4% |
| 44 | 0.25 | 9 | 250 | 55.8% | 42.0% | 0.5% | 0.0% | 40.9% | 96.2% | 0.8% |
| 45 | 0.25 | 9 | 275 | 73.6% | 24.5% | 0.3% | 0.0% | 60.7% | 97.4% | 0.3% |
| 46 | 0.25 | 9 | 300 | 76.6% | 21.9% | 0.3% | 0.0% | 64.1% | 98.1% | 0.4% |
| 47 | 0.25 | 9 | 325 | 75.3% | 19.7% | 2.4% | 0.4% | 67.2% | 94.2% | 3.0% |
| 48 | 0.25 | 9 | 350 | 69.9% | 13.3% | 12.3% | 0.4% | 76.7% | 80.9% | 14.2% |
| 49 | 0.5 | 9 | 200 | 59.5% | 37.9% | 0.3% | 0.0% | 45.0% | 95.9% | 0.5% |
| 50 | 0.5 | 9 | 225 | 70.2% | 27.0% | 0.6% | 0.4% | 57.6% | 96.6% | 0.8% |
| 51 | 0.5 | 9 | 250 | 72.3% | 25.6% | 0.8% | 0.0% | 59.2% | 97.2% | 1.1% |
| 52 | 0.5 | 9 | 275 | 72.5% | 24.7% | 1.0% | 0.0% | 60.4% | 96.2% | 1.4% |
| 53 | 0.5 | 9 | 300 | 72.3% | 23.9% | 1.4% | 0.0% | 61.4% | 94.9% | 1.8% |
| 54 | 0.5 | 9 | 325 | 72.8% | 22.5% | 2.3% | 0.0% | 63.2% | 94.0% | 2.9% |
| 55 | 0.5 | 9 | 350 | 70.7% | 18.8% | 4.0% | 0.0% | 68.3% | 87.1% | 4.9% |
| 56 | 1.0 | 9 | 200 | 45.7% | 51.7% | 0.5% | 0.0% | 31.8% | 94.6% | 1.0% |
| 57 | 1.0 | 9 | 225 | 68.8% | 28.0% | 0.4% | 0.0% | 56.3% | 95.5% | 0.5% |
| 58 | 1.0 | 9 | 250 | 73.5% | 23.7% | 0.9% | 0.4% | 61.8% | 96.7% | 1.2% |
| 59 | 1.0 | 9 | 275 | 74.7% | 22.8% | 0.9% | 0.0% | 62.9% | 96.8% | 1.2% |
| 60 | 1.0 | 9 | 300 | 75.4% | 22.0% | 1.2% | 0.0% | 63.9% | 96.7% | 1.5% |
| 61 | 1.0 | 9 | 325 | 74.3% | 20.5% | 1.9% | 0.0% | 65.9% | 93.4% | 2.4% |
| 62 | 1.0 | 9 | 350 | 74.4% | 18.2% | 4.0% | 0.0% | 69.2% | 91.0% | 4.9% |

The catalyst achieved the predicted equilibrium conversions at temperatures above 267° C. Higher temperatures resulted in higher conversion of DMS, in accord with the equilibrium constraints of the cleavage reaction. The selectivity of DMS to CS$_2$ is less than 2% for temperatures below 300° C. The data shows that increasing the H$_2$S/DMS mole ratio increases the conversion of DMS to MeSH while minimizing CS$_2$ formation. Varying the WHSV seemed to have little effect on the conversion of DMS to MeSH; although, slightly lower amounts CS$_2$ were formed at lower WHSVs.

Further discussion of the data in Example 1 is provided in Example 2.

Example 2

In Example 2, a single run having a duration of fifteen days was conducted for a standalone DMS cleavage system and process. A stainless steel reactor 300 configured as shown in FIG. 5 was used for the DMS cleavage process. The reactor 300 was tubular in shape, having a diameter D of 1.939 inches (4.925 cm) and a length L of 48.5 (123.2 cm) inches.

The CoMo catalyst used in the catalyst beds 314, 316, and 318 of Example 2 was a 3% Co, 10% Mo, alumina supported refinery HDS catalyst. The catalyst of CoMo on an alumina support (CoMo catalyst) was in the form of 0.05 inch (1.27 mm) extrudates. 14-20 mesh alpha alumina (ALUNDUM® alumina) spherical particles were also utilized in catalyst beds 312, 314, and 316. As shown in FIG. 5, a first catalyst bed (or top zone) 312 contained 14-20 mesh alpha alumina with no CoMo catalyst, a second catalyst bed (or 2$^{nd}$ zone) 314 was 122 g of the CoMo catalyst diluted (mixed) with 243 g of 14-20 mesh alpha alumina, a third catalyst bed (or 3$^{rd}$ zone) 316 was 158 g of the CoMo catalyst diluted (mixed) with 158 g of the 14-20 mesh alpha alumina, and a fourth catalyst bed (or bottom zone) 318 was 224 g of the CoMo catalyst with no 14-20 mesh alpha alumina. The first and second catalyst beds 312 and 314 were separated by steel wool 322; the second and third catalyst beds 314 and 316 were separated by steel wool 324; and the third and fourth catalyst beds 316 and 318 were likewise separated by steel wool 326. A layer of steel wool and beads 328 covered the fourth catalyst bed 318 on the side facing the reactor inlet 302.

During the run, the reactor 300 was heated using an external electric furnace 330 with three heating zones, top furnace zone 332, middle furnace zone 334, and bottom furnace zone 336.

Temperatures were measured and controlled using thermocouples 340, 341, 342, 343, 344, and 345 placed in each of the furnace zones 332, 334, and 336 as shown in FIG. 5. Thermocouples were also placed in each catalyst bed 312, 314, 316, and 318. In the first catalyst bed 312, a thermocouple was placed 31 inches from the reactor inlet 302. In the second catalyst bed 314, the thermocouple was placed 22 inches from the reactor inlet 302. In the third catalyst bed 316, a thermocouple was placed 15 inches from the reactor inlet 302. In the fourth catalyst bed 318, a thermocouple was placed 10 inches from the reactor inlet 302.

A H$_2$S feed and a DMS feed were connected to the reactor inlet 302. A WHSV of 1 g DMS/g cat./hr and a weight ratio of 15:1 for H$_2$S/DMS were used for the entirety of the run.

Data for the run of Example 2 are shown in the Tables below:

TABLE 2

Reactor Feed Composition

| Mole H$_2$S | Moles DMS | Mole % H$_2$S | Mole % DMS | Mole Ratio H$_2$S/DMS | Mass Ratio H$_2$S/DMS |
|---|---|---|---|---|---|
| 2.41 | 0.11 | 95.49 | 4.51 | 21.2:1 | 15:1 |

TABLE 3

Weight Response Factor and Molecular Weight

| | Weight Response Factor | Molecular Weight (g/mol) |
|---|---|---|
| H$_2$S | 0.89 | 34.08 |
| MeSH | 0.81 | 62.13 |

TABLE 3-continued

Weight Response Factor and Molecular Weight

| | Weight Response Factor | Molecular Weight (g/mol) |
|---|---|---|
| DMS | 0.80 | 48.11 |
| $CS_2$ | 0.82 | 76.13 |

TABLE 4

Standalone DMS Cleavage Process 15-hour Temperature Data

| | Measurement No. | | | | | | | | | | |
|---|---|---|---|---|---|---|---|---|---|---|---|
| | 1 | 2 | 3 | 4 | 5 | 6 | 7 | 8 | 9 | 10 | 11 |
| Hours On-line (hr) | 10 | 34 | 54 | 78 | 102 | 126 | 150.5 | 171 | 195 | 219 | 239 |
| Top Furnace Zone (° C.) | 295 | 285 | 290 | 295 | 292 | 291 | 294 | 299 | 306 | 311 | 311 |
| Middle Furnace Zone (° C.) | 277 | 280 | 274 | 276 | 273 | 277 | 274 | 278 | 242 | 283 | 282 |
| Bottom Furnace Zone (° C.) | 265 | 261 | 269 | 273 | 275 | 274 | 274 | 276 | 290 | 280 | 282 |
| 31" Top Zone Alundum ® alumina (° C.) | 311 | 267 | 293 | 293 | 290 | 244 | 290 | 295 | 284 | 302 | 298 |
| 22" $2^{nd}$ Zone (° C.) | 314 | 303 | 308 | 305 | 306 | 279 | 305 | 307 | 262 | 315 | 313 |
| 15" $3^{rd}$ Zone (° C.) | 327 | 322 | 330 | 331 | 332 | 310 | 332 | 334 | 268 | 324 | 323 |
| 10" Bottom Zone (° C.) | 257 | 310 | 305 | 311 | 307 | 307 | 310 | 310 | 244 | 305 | 307 |
| WAT (° C.) | 299 | 312 | 314 | 316 | 315 | 299 | 316 | 317 | 258 | 315 | 314 |

TABLE 5

15-hour Run Data

| | | | Sample No. | | | | | | | |
|---|---|---|---|---|---|---|---|---|---|---|
| | | Feed | 1 | 2 | 3 | 6 | 10 | 13 | 15 | 16 |
| Hours On-line | (hr) | — | 9.5 | 31 | 37 | 75 | 147 | 174 | 193 | 215 |
| DMS Conversion | (%) | — | 72.50 | 67.31 | 71.23 | 71.40 | 80.54 | 68.19 | 71.68 | 66.39 |
| GC Areas | $H_2S$ | 92.12 | 63.05 | 60.15 | 64.99 | 82.86 | 87.51 | 72.01 | 86.31 | 75.34 |
| | MeSH | — | 25.89 | 25.89 | 24.34 | 11.25 | 8.86 | 19.22 | 9.89 | 16.05 |
| | DMS | 6.83 | 8.36 | 10.87 | 8.32 | 3.88 | 1.86 | 7.43 | 3.13 | 6.72 |
| | $CS_2$ | — | 2.69 | 2.45 | 2.35 | 1.34 | 1.16 | 1.33 | 0.26 | 1.07 |
| Wt % | $H_2S$ | 81.99 | 56.11 | 53.53 | 57.84 | 73.75 | 77.88 | 64.09 | 76.82 | 67.05 |
| | MeSH | — | 20.97 | 21.49 | 19.72 | 9.11 | 7.18 | 15.57 | 8.01 | 13.00 |
| | DMS | 5.46 | 6.69 | 8.70 | 6.66 | 3.10 | 1.49 | 5.94 | 2.50 | 5.38 |
| | $CS_2$ | — | 2.21 | 2.01 | 1.93 | 1.10 | 0.95 | 1.09 | 0.21 | 0.88 |
| Normalized Wt % | MeSH | — | 70.22 | 66.75 | 69.67 | 68.44 | 74.63 | 68.88 | 74.67 | 67.52 |
| | DMS | — | 22.39 | 27.01 | 23.52 | 23.31 | 15.47 | 26.30 | 23.34 | 27.92 |
| | $CS_2$ | — | 7.39 | 6.24 | 6.81 | 8.25 | 9.89 | 4.83 | 1.99 | 4.56 |
| Normalized Moles | MeSH | — | 1.13 | 1.07 | 1.12 | 1.10 | 1.20 | 1.11 | 1.20 | 1.09 |
| | DMS | — | 0.47 | 0.56 | 0.49 | 0.48 | 0.32 | 0.55 | 0.49 | 0.58 |
| | $CS_2$ | — | 0.10 | 0.08 | 0.09 | 0.11 | 0.13 | 0.06 | 0.03 | 0.06 |
| Normalized Mole % | MeSH | — | 66.77 | 62.54 | 65.97 | 65.00 | 72.68 | 64.50 | 70.15 | 62.93 |
| | DMS | — | 27.50 | 32.69 | 28.77 | 28.60 | 19.46 | 31.81 | 28.32 | 33.61 |
| | $CS_2$ | — | 5.73 | 4.77 | 5.26 | 6.40 | 7.86 | 3.69 | 1.52 | 3.47 |

The range of temperatures for $T_{inlet}$ which provide favorable reactions are temperatures of 250° C. or greater. The range of temperatures for $T_{outlet}$ which provide favorable reactions are temperatures of 305° C. or less. At higher temperatures, the selectivity of DMS to MeSH decreased and the amount of $CS_2$ formed increased.

The above data for both Example 1 and Example 2 demonstrate ranges for various parameters which are effective for DMS conversion to MeSH. For example, the WAT can range from about 265° C. to about 305° C. The $H_2S$/DMS mole ratio can be at least 3:1, at least 5:1, or at least 10:1 and less than 100:1. The WHSV can range from 0.2 to 15 g DMS/g cat./hr; alternatively, 1 to 2 g DMS/g cat./hr.

A WAT of about 285° C. can produce favorable operating conditions for DMS cleavage to produce MeSH. Further favorable conditions can be achieved when using a WAT of about 285° C. in combination with a pressure of 500 psig (3447 kPa), a WHSV of 1.5 g DMS/g cat./hr, and a mole ratio of $H_2S$ to DMS of 10:1. Of course, the WAT, pressure, WHSV, and mole ratio can be at different values while achieving the efficient integration with a MeSH production plant.

The above data also indicate that MeSH should be excluded from being fed to the DMS cleavage reactor.

Example 3

Example 3 provides stream compositions of a typical process plant for the production of MeSH by reacting methanol and hydrogen sulfide. Table 6 shows the operating conditions and composition of the various streams obtained from the process plant. The stream data was obtained from a simulation using Aspen Plus V8.6.

TABLE 6

MeSH Production Plant Stream Data

| | Feed Streams | | Purge Streams | | | Product Streams | |
|---|---|---|---|---|---|---|---|
| | H$_2$S | MeOH | Vent | Water | Heavies | MeSH | DMS |
| Mole Flow (lbmol/hr) | 385 | 410 | 14 | 409 | 4 | 342 | 30 |
| Mass Flow lb/hr (kg/hr) | 13014 (5903) | 13119 (5951) | 285 (129.5) | 7363 (3340) | 288 (12.7) | 16450 (7462) | 1844 (836) |
| Temp °F. (°C.) | 130 (54.4) | 60 (15.6) | 73 (22.8) | 97 (36.1) | 110 (43.3) | 100 (37.8) | 104 (40) |
| Pressure psia (kPa) | 115 (793) | 30 (207) | 49 (338) | 425 (2930) | 50 (345) | 150 (1034) | 510 (1034) |
| Vapor Fraction | 1 | 0 | 1 | 0 | 0 | 0 | 0 |
| Component Mole Fraction | | | | | | | |
| H$_2$ | 0.008 | 0.000 | 0.44 | 0.000 | 0.000 | 0.000 | 0.000 |
| METHANE | 0.000 | 0.000 | 0.03 | 0.000 | 0.000 | 0.000 | 0.000 |
| CO$_2$ | 0.000 | 0.000 | 0.03 | 0.000 | 0.000 | 0.000 | 0.000 |
| H$_2$S | 0.991 | 0.000 | 0.39 | 0.000 | 0.000 | 0.000 | 0.000 |
| MESH | 0.000 | 0.000 | 0.07 | 0.000 | 0.000 | 0.998 | 0.019 |
| DMS | 0.000 | 0.000 | 0.000 | 0.000 | 0.487 | 0.002 | 0.980 |
| METHANOL | 0.000 | 0.998 | 0.03 | 0.000 | 0.000 | 0.000 | 0.000 |
| WATER | 0.000 | 0.002 | 0.000 | 1.000 | 0.000 | 0.000 | 0.000 |
| DMDS | 0.000 | 0.000 | 0.000 | 0.000 | 0.510 | 0.000 | 0.001 |
| CS$_2$ | 0.000 | 0.000 | 0.000 | 0.000 | 0.001 | 0.000 | 0.000 |
| Component Mass Fraction | | | | | | | |
| H$_2$ | 0.001 | 0.000 | 0.04 | 0.000 | 0.000 | 0.000 | 0.000 |
| METHANE | 0.000 | 0.000 | 0.03 | 0.000 | 0.000 | 0.000 | 0.000 |
| CO$_2$ | 0.000 | 0.000 | 0.06 | 0.000 | 0.000 | 0.000 | 0.000 |
| H$_2$S | 0.999 | 0.000 | 0.64 | 0.000 | 0.000 | 0.000 | 0.000 |
| MESH | 0.000 | 0.000 | 0.17 | 0.000 | 0.000 | 0.998 | 0.014 |
| DMS | 0.000 | 0.000 | 0.000 | 0.000 | 0.386 | 0.002 | 0.984 |
| METHANOL | 0.000 | 0.999 | 0.05 | 0.000 | 0.000 | 0.000 | 0.000 |
| WATER | 0.000 | 0.001 | 0.000 | 1.000 | 0.000 | 0.000 | 0.000 |
| DMDS | 0.000 | 0.000 | 0.000 | 0.000 | 0.612 | 0.000 | 0.001 |
| CS$_2$ | 0.000 | 0.000 | 0.000 | 0.000 | 0.001 | 0.000 | 0.001 |

As can be seen in Table 6, the MeSH production plant can produce a MeSH stream in a liquid phase having a mole flow of 342 lbmol/hr, a mass flow of 16,450 lb/hr (7,462 kg/hr), a temperature of 100° F. (37.8° C.), and a pressure of 150 psia (1,034 kPa). The components in the MeSH stream include 0.998 MeSH (based on both mole fraction and mass fraction) and 0.002 DMS (again based on both mole fraction and mass fraction).

The DMS stream produced by the MeSH production plant can be in liquid phase and have a mole flow of 30 lbmol/hr, a mass flow of 1,844 lb/hr (836 kg/hr), a temperature of 104° F. (40° C.), and a pressure of 510 psia (3,516 kPa). The mole fraction of components in the DMS stream includes 0.019 MeSH, 0.980 DMS, and 0.001 dimethyl disulfide (DMDS). The mass fraction of components in the DMS stream includes 0.014 MeSH, 0.984 DMS, 0.001 DMDS, and 0.001 carbon disulfide (CS$_2$).

Example 4

Example 4 shows stream data for a methyl mercaptan production plant which is combined with a DMS cleavage process as described herein (the combined plant is referred to as the "integrated MeSH production plant") and shown in FIG. 3. The stream data was obtained from a simulation using Aspen Plus V8.6.

TABLE 7A

Stream Data for an Integrated MeSH Production Plant

| | Stream No. from FIG. 3 | | | | | |
|---|---|---|---|---|---|---|
| | 202 | 204 | 104 | 102 | 106 | 108 |
| Temperature °F. (°C.) | 130 (54.4) | 60 (15.6) | 97 (36.1) | 105 (40.6) | 101 (38.3) | 545 (285) |
| Pressure psia (kPa) | 115 (793) | 30 (207) | 540 (3723) | 520 (3585) | 520 (3585) | 505 (3482) |
| Vapor Fraction | 1 | 0 | 0 | 0 | 0 | 1 |
| Component Mole Fraction | | | | | | |
| H$_2$ | 0.000 | 0.000 | 0.000 | 0.000 | 0.000 | 0.000 |
| METHANE | 0.000 | 0.000 | 0.007 | 0.000 | 0.006 | 0.006 |
| CO$_2$ | 0.000 | 0.000 | 0.004 | 0.000 | 0.003 | 0.003 |
| H$_2$S | 1.000 | 0.000 | 0.989 | 0.000 | 0.896 | 0.896 |

TABLE 7A-continued

Stream Data for an Integrated MeSH Production Plant

Stream No. from FIG. 3

|  | 202 | 204 | 104 | 102 | 106 | 108 |
|---|---|---|---|---|---|---|
| MESH | 0.000 | 0.000 | 0.000 | 0.030 | 0.003 | 0.003 |
| DMS | 0.000 | 0.000 | 0.000 | 0.957 | 0.090 | 0.090 |
| METHANOL | 0.000 | 1.000 | 0.000 | 0.000 | 0.000 | 0.000 |
| WATER | 0.000 | 0.000 | 0.000 | 0.000 | 0.000 | 0.000 |
| DMDS | 0.000 | 0.000 | 0.000 | 0.000 | 0.000 | 0.000 |
| $CS_2$ | 0.000 | 0.000 | 0.000 | 0.013 | 0.001 | 0.001 |

TABLE 7B

Stream Data for an Integrated MeSH Production Plant

Stream No. from FIG. 3

|  | 110 | 112 | 220 | 206 | 208 | 209 |
|---|---|---|---|---|---|---|
| Temperature °F. (°C.) | 545 (285) | 200 (93.3) | 100 (37.8) | 73 (22.8) | 110 (43.3) | 97 (36.1) |
| Pressure psia (kPa) | 478 (3296) | 468 (3227) | 150 (1034) | 40 (276) | 50 (345) | 425 (3103) |
| Vapor Fraction | 1 | 1 | 0 | 1 | 0 | 0 |
| Component Mole Fraction | | | | | | |
| $H_2$ | 0.001 | 0.001 | 0.000 | 0.296 | 0.000 | 0.000 |
| METHANE | 0.007 | 0.007 | 0.000 | 0.065 | 0.000 | 0.000 |
| $CO_2$ | 0.003 | 0.003 | 0.000 | 0.032 | 0.000 | 0.000 |
| $H_2S$ | 0.838 | 0.838 | 0.000 | 0.442 | 0.000 | 0.000 |
| MESH | 0.116 | 0.116 | 0.998 | 0.105 | 0.000 | 0.000 |
| DMS | 0.032 | 0.032 | 0.002 | 0.002 | 0.388 | 0.000 |
| METHANOL | 0.000 | 0.000 | 0.000 | 0.058 | 0.000 | 0.000 |
| WATER | 0.000 | 0.000 | 0.000 | 0.000 | 0.000 | 1.000 |
| DMDS | 0.000 | 0.000 | 0.000 | 0.000 | 0.510 | 0.000 |
| $CS_2$ | 0.002 | 0.002 | 0.000 | 0.000 | 0.102 | 0.000 |

As can be seen in Table 7B, the MeSH production plant 210 integrated with the DMS cleavage system 100 disclosed herein can produce a MeSH product stream 220 in a liquid phase having a temperature of 100° F. (37.8° C.), a pressure of 150 psia (1,034 kPa), and in liquid phase. The components in the MeSH product stream 220 include 0.998 MeSH mole fraction and 0.002 DMS mole fraction.

The overall mass balance of the integrated process plant in Tables 7A and 7B shows that there is essentially no $CS_2$ found (less than about 5 ppmw $CS_2$ based on weight of the MeSH product stream 220) in the final MeSH product stream 220 and that any $CS_2$ that is formed in the plant leaves the plant in the organic liquid purge stream 208. The less-than-20 ppmw specification typically required for MeSH product is readily met in the integrated process.

Example 5

Example 5 shows stream data for a methyl mercaptan production plant 210 which is combined with a DMS cleavage system 100 as described herein and illustrated in FIG. 4. The stream data was obtained from a simulation using Aspen Plus V8.6.

TABLE 8

Stream Data for an Integrated MeSH Production Plant

Stream No. from FIG. 4

|  | Feed Streams | | Purge Streams | | | MeSH Product |
|---|---|---|---|---|---|---|
|  | 202 | 204 | 206 | 209 | 208 | 220 |
| Mole Flow lbmol/hr | 391 | 390 | 11 | 389 | 4 | 380 |
| Mass Flow lb/hr (kg/hr) | 13341 (6371) | 12500 (5951) | 275 (125) | 7004 (3178) | 283 (128) | 18279 (8291) |
| Temp °F. (°C.) | 130 (54.4) | 60 (15.6) | 73 (22.8) | 97 (36.1) | 110 (43.3) | 100 (37.8) |
| Pressure psia (kPa) | 115 (793) | 30 (207) | 40 (276) | 425 (2930) | 50 (345) | 150 (1034) |
| Vapor Fraction | 1 | 0 | 1 | 0 | 0 | 0 |

TABLE 8-continued

Stream Data for an Integrated MeSH Production Plant

Stream No. from FIG. 4

| | Feed Streams | | Purge Streams | | | MeSH Product |
|---|---|---|---|---|---|---|
| | 202 | 204 | 206 | 209 | 208 | 220 |
| Component Mole Fraction | | | | | | |
| $H_2$ | 0.000 | 0.000 | 0.295 | 0.000 | 0.000 | 0.000 |
| METHANE | 0.000 | 0.000 | 0.065 | 0.000 | 0.000 | 0.000 |
| $CO_2$ | 0.000 | 0.000 | 0.032 | 0.000 | 0.000 | 0.000 |
| $H_2S$ | 0.991 | 0.000 | 0.442 | 0.000 | 0.000 | 0.000 |
| MESH | 0.000 | 0.000 | 0.105 | 0.000 | 0.000 | 0.998 |
| DMS | 0.000 | 0.000 | 0.059 | 0.000 | 0.388 | 0.002 |
| METHANOL | 0.000 | 0.998 | 0.000 | 0.059 | 0.000 | 0.000 |
| WATER | 0.000 | 0.002 | 0.000 | 1.000 | 0.000 | 0.000 |
| DMDS | 0.000 | 0.000 | 0.000 | 0.000 | 0.510 | 0.000 |
| $CS_2$ | 0.000 | 0.000 | 0.000 | 0.000 | 0.102 | 0.000 |
| Component Mass Fraction | | | | | | |
| $H_2$ | 0.001 | 0.000 | 0.024 | 0.000 | 0.000 | 0.000 |
| METHANE | 0.000 | 0.000 | 0.041 | 0.000 | 0.000 | 0.000 |
| $CO_2$ | 0.000 | 0.000 | 0.056 | 0.000 | 0.000 | 0.000 |
| $H_2S$ | 0.999 | 0.000 | 0.599 | 0.000 | 0.000 | 0.000 |
| MESH | 0.000 | 0.000 | 0.202 | 0.000 | 0.000 | 0.998 |
| DMS | 0.000 | 0.000 | 0.005 | 0.000 | 0.302 | 0.002 |
| METHANOL | 0.000 | 0.999 | 0.074 | 0.000 | 0.000 | 0.000 |
| WATER | 0.000 | 0.001 | 0.000 | 1.000 | 0.000 | 0.000 |
| DMDS | 0.000 | 0.000 | 0.000 | 0.000 | 0.601 | 0.000 |
| $CS_2$ | 0.000 | 0.000 | 0.000 | 0.000 | 0.097 | 0.000 |

As can be seen in Table 8, the MeSH production plant 210 integrated with the DMS cleavage system 100 can produce a MeSH product stream 220 in a liquid phase having a mole flow of 380 lbmol/hr, a mass flow of 18,279 lb/hr (8,291 kg/hr), a temperature of 100° F. (37.8° C.), and a pressure of 150 psia (1,034 kPa). The components in the MeSH product stream 220 include 0.998 MeSH (based on both mole fraction and mass fraction) and 0.002 DMS (again based on both mole fraction and mass fraction).

Comparing the MeSH product to methanol feed ratios in Tables 6 and 8 (Table 6: 16,450/13,119=1.25 lb MeSH/lb methanol and Table 8: 18,279/12,500=1.46 lb MeSH/lb methanol) shows that the integrated system produces 1.46 lb MeSH product per lb of methanol feed, which is a significant improvement over the 1.25 lb of MeSH product produced per lb of methanol feed in the stand-alone MeSH plant.

The overall mass balance of the integrated plant 210 in Table 8 shows that there is essentially no $CS_2$ found (less than about 5 ppmw $CS_2$ based on weight of the MeSH stream) in the final MeSH product stream 220 and that any $CS_2$ that is formed in the plant 210 leaves the plant 210 from a single source (a heavies purge stream). The less-than-20 ppmw specification typically required for MeSH product is readily met.

Comparing the MeSH stream of the typical MeSH production plant with the MeSH stream from the integrated MeSH production plant, a higher production of on-spec MeSH is enabled by integrating the DMS cleavage process with the MeSH production plant. Any differences in the other plant outlet streams in the integrated MeSH production plant are minimal.

ADDITIONAL DISCLOSURE

The following is provided as additional disclosure for combinations of features and aspects of the present invention.

Aspect 1 is a process for the conversion of dimethyl sulfide to methyl mercaptan, comprising:

contacting dimethyl sulfide with a catalyst in the presence of an excess amount of hydrogen sulfide in a reactor to yield a reactor effluent comprising methyl mercaptan, hydrogen sulfide, and carbon disulfide, wherein the catalyst comprises alumina, NiMo on an alumina support, CoMo on an alumina support, or a combination thereof.

Aspect 2 is the process of aspect 1, wherein carbon disulfide is present in the reactor effluent in an amount of less than about 2 mole % based on a total moles of methyl mercaptan, hydrogen sulfide, dimethyl disulfide, and carbon disulfide in the reactor effluent.

Aspect 3 is the process of any one of aspects 1-2, wherein the step of contacting has a conversion of dimethyl sulfide of greater than 50% and a selectivity to methyl mercaptan of greater than 95%.

Aspect 4 is the process of any one of aspects 1-3, further comprising:

separating the reactor effluent into a recycle $H_2S$ stream and a methyl mercaptan stream; and recycling the recycle $H_2S$ stream for use in the step of contacting.

Aspect 5 is the process of any one of aspects 1-4, wherein the step of contacting is performed at a hydrogen sulfide to dimethyl sulfide mole ratio of at least 3:1.

Aspect 6 is the process of any one of aspects 1-5, wherein the step of contacting is performed at a weight average temperature in a range of from about 265° C. to about 305° C.

Aspect 7 is the process of any one of aspects 1-6, wherein the step of contacting is performed at a weight hourly space velocity of about 0.2 to about 15 g dimethyl sulfide/g cat./hr.

Aspect 8 is the process of any one of aspects 1-7, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

Aspect 9 is the process of any one of aspects 1-8, further comprising:

combining hydrogen sulfide and dimethyl sulfide received from a methyl mercaptan production plant to yield a combined feed stream comprising hydrogen sulfide and dimethyl sulfide.

Aspect 10 is process of any one of aspects 1-9, further comprising:

feeding the hydrogen sulfide and dimethyl sulfide to the reactor, optionally via the combined feed stream of aspect 9.

Aspect 11 is the process of aspect 10, wherein one or more purge streams of the methyl mercaptan production plant comprises dimethyl sulfide in an amount which is less than about 5 wt % based on the weight of dimethyl sulfide fed to the reactor.

Aspect 12 is the process of any one of aspects 10-11, wherein the step of feeding comprises:

preheating the combined feed stream in a cross-flow heat exchanger using the reactor effluent as a heat transfer medium to yield a heated feed stream; and flowing the heated feed stream to the reactor.

Aspect 13 is the process of any one of aspects 1-12, further comprising:

flowing a $H_2S$ stream comprising hydrogen sulfide to the reactor, wherein the hydrogen sulfide in the $H_2S$ stream is received from a methyl mercaptan production plant; and flowing a DMS stream comprising dimethyl sulfide to the DMS cleavage reactor, wherein the dimethyl sulfide in the DMS stream is received from the methyl mercaptan production plant.

Aspect 14 is the process of any one of aspects 1-13, further comprising:

cooling the reactor effluent to yield a cooled reactor effluent; and recycling the cooled reactor effluent to a methyl mercaptan production plant.

Aspect 15 is the process of any one of aspects 9, 11, 13, and 14, further comprising:

recovering a MeSH product stream comprising methyl mercaptan from the methyl mercaptan production plant, wherein the MeSH product stream further comprises less than about 5 ppmw carbon disulfide based on a total weight of the MeSH product stream.

Aspect 16 is the process of any one of aspects 9, 11, and 13-15, further comprising:

recovering one or more purge streams from the methyl mercaptan production plant, wherein the one or more purge streams comprises equal to or less than about 10 mole % carbon disulfide based on a total moles in the one or more purge streams.

Aspect 17 is the process of any one of aspects 1-13 and 15-16, further comprising:

cooling the reactor effluent to yield a cooled reactor effluent;

separating the cooled reactor effluent into an enriched $H_2S$ stream comprising hydrogen sulfide and an enriched MeSH stream comprising methyl mercaptan; and recycling the methyl mercaptan in the enriched MeSH stream to a methyl mercaptan production plant separately from recycling the hydrogen sulfide in the enriched $H_2S$ stream to the methyl mercaptan production plant.

Aspect 18 is a system comprising:

a DMS stream comprising dimethyl sulfide received from a methyl mercaptan production plant;

a $H_2S$ stream comprising hydrogen sulfide received from the methyl mercaptan production plant;

a combined feed stream comprising dimethyl sulfide received from the DMS stream and hydrogen sulfide received from the $H_2S$ stream;

a preheater which receives the combined feed stream and yields a heated feed stream comprising the dimethyl sulfide and hydrogen sulfide at a reaction temperature;

a reactor receiving the heated feed stream, wherein the reactor contains a catalyst comprising alumina, NiMo on an alumina support, CoMo on an alumina support, or a combination thereof;

a reactor effluent stream receiving reactor effluent from the reactor, wherein the reactor effluent comprises methyl mercaptan in an amount of about 5 mole % to about 76 mole % based on the total moles of methyl mercaptan, dimethyl sulfide, carbon disulfide, and dimethyl disulfide in the reactor effluent stream.

Aspect 19 is the system of aspect 18, wherein the reactor effluent is cooled to yield a cooled reactor effluent stream.

Aspect 20 is the system of aspect 19, wherein the cooled reactor effluent stream recycles methyl mercaptan and hydrogen sulfide to the methyl mercaptan production plant.

Aspect 21 is the system of any one of aspects 18-20, further comprising:

a MeSH product stream comprising methyl mercaptan and less than about 5 ppmw carbon disulfide based on a total weight of the MeSH product stream, wherein the methyl mercaptan is recovered from the methyl mercaptan production plant.

Aspect 22 is the system of any one of aspects 18-21, further comprising:

one or more purge streams comprising equal to or less than about 10 mole % carbon disulfide based on a total moles in the one or more purge streams, wherein the one or more purge streams is recovered from the methyl mercaptan production plant.

Aspect 23 is the system of aspect 22, wherein the one or more purge streams comprises dimethyl sulfide in an amount which is less than about 5 wt % based on the weight of dimethyl sulfide in the DMS stream.

Aspect 24 is the system of any one of aspects 19-23, further comprising:

a separation vessel, wherein the cooled reactor effluent stream recycles methyl mercaptan and hydrogen sulfide to the separation vessel;

an enriched $H_2S$ stream flowing hydrogen sulfide from the separation vessel, wherein the hydrogen sulfide recycles to the methyl mercaptan production plant via in the enriched $H_2S$ stream; and an enriched MeSH stream flowing methyl mercaptan from the separation vessel, wherein the methyl mercaptan recycles to the methyl mercaptan production plant via the enriched MeSH stream.

Aspect 25 is a process comprising:

utilizing a methyl mercaptan production plant to recover dimethyl sulfide;

responsive to a first market condition, contacting at least a portion of the recovered dimethyl sulfide with a CoMo or NiMo catalyst in the presence of hydrogen sulfide in a reactor to yield a reactor effluent comprising methyl mercaptan, hydrogen sulfide, and carbon disulfide;

responsive to a second market condition, discontinuing the contacting of the recovered dimethyl sulfide in the reactor; and selling all or a portion of the recovered dimethyl sulfide.

While aspects and embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_1+k*(R_u-R_1)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention.

What is claimed is:

1. A process for conversion of dimethyl sulfide to methyl mercaptan, comprising:
    contacting dimethyl sulfide in a combined feed stream with a catalyst in the presence of an excess amount of hydrogen sulfide in a reactor to yield a reactor effluent comprising methyl mercaptan, hydrogen sulfide, and carbon disulfide, wherein the catalyst consists of NiMo on an alumina support; CoMo on an alumina support; NiMO on an alumina support and CoMo on an alumina support; NiMo on an alumina support and alumina; CoMo on an alumina support and alumina; or NiMo on an alumina support, CoMo on an alumina support, and alumina;
    wherein the step of contacting in a single pass through the reactor has, in the reactor effluent, a conversion of dimethyl sulfide of greater than 50% and a selectivity to methyl mercaptan of greater than 95%,
    wherein carbon disulfide is present in the reactor effluent in an amount of less than about 2 mole% based on a total moles of methyl mercaptan, hydrogen sulfide, dimethyl disulfide, and carbon disulfide in the reactor effluent.

2. The process of claim 1, further comprising:
    separating the reactor effluent into a recycle $H_2S$ stream and a methyl mercaptan stream; and
    recycling the recycle $H_2S$ stream for use in the step of contacting.

3. The process of claim 1, wherein the step of contacting is performed at a hydrogen sulfide to dimethyl sulfide mole ratio of at least 3:1 and less than 100:1.

4. The process of claim 1, wherein the step of contacting is performed at a weight average temperature in a range of from about 265° C. to about 305° C.

5. The process of claim 1, wherein the step of contacting is performed at a weight hourly space velocity of about 0.2 to about 15 g dimethyl sulfide/g cat./hr.

6. The process of claim 1, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

7. The process of claim 1, further comprising;
    combining hydrogen sulfide and dimethyl sulfide received from a methyl mercaptan production plant to yield a combined feed stream comprising hydrogen sulfide and dimethyl sulfide; and
    feeding the hydrogen sulfide and dimethyl sulfide to the reactor via the combined feed stream.

8. The process of claim 7, wherein one or more purge streams of the methyl mercaptan production plant comprises dimethyl sulfide in an amount which is less than about 5 wt% based on a weight of dimethyl sulfide fed to the reactor.

9. The process of claim 7, wherein the step of feeding comprises:
    preheating the combined feed stream in a cross-flow heat exchanger using the reactor effluent as a heat transfer medium to yield a heated feed stream; and
    flowing the heated feed stream to the reactor.

10. The process of claim 1, further comprising:
    flowing a $H_2S$ stream comprising hydrogen sulfide to the reactor, wherein the hydrogen sulfide in the $H_2S$ stream is received from a methyl mercaptan production plant; and
    flowing a DMS stream comprising dimethyl sulfide to the DMS cleavage reactor, wherein the dimethyl sulfide in the DMS stream is received from the methyl mercaptan production plant.

11. The process of claim 1, further comprising:
    cooling the reactor effluent to yield a cooled reactor effluent; and
    recycling the cooled reactor effluent to a methyl mercaptan production plant.

12. The process of claim 11, further comprising:
    recovering a MeSH product stream comprising methyl mercaptan from the methyl mercaptan production plant, wherein the MeSH product stream farther comprises less than about 5 ppmw carbon disulfide based on a total weight of the MeSH product stream.

13. The process of claim 12, further comprising:
    recovering one or more purge streams from the methyl mercaptan production plant, wherein the one or more purge streams comprises equal to or less than about 10 mole% carbon disulfide based on a total moles in the one or more purge streams.

14. The process of claim 1, further comprising:
cooling the reactor effluent to yield a cooled reactor effluent;
separating the cooled reactor effluent into an enriched $H_2S$ stream comprising hydrogen sulfide and an enriched MeSH stream comprising methyl mercaptan; and
recycling the methyl mercaptan in the enriched MeSH stream to a methyl mercaptan production plant separately from recycling the hydrogen. sulfide in the enriched $H_2S$ stream to the methyl mercaptan production plant.

15. The process of claim 1, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

16. The process of claim 2, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

17. The process of claim 7, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

18. The process of claim 8, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

19. The process of claim 9, wherein the step of contacting is performed at a hydrogen sulfide dimethyl sulfide mole ratio of about 10:1, a weight hourly space velocity of about 1.5 g dimethyl sulfide/g cat./hr, and a weight average temperature of about 285° C.

20. The process of claim 10, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

21. The process of claim 11, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

22. The process of claim 12, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

23. The process of claim 14, wherein the step of contacting is performed at a hydrogen sulfide to dimethyl sulfide mole ratio of about 10:1, a weight hourly space velocity of about 1.5 g dimethyl sulfide/g cat./hr, and a weight average temperature of about 285° C.

* * * * *